(12) United States Patent
Clifton et al.

(10) Patent No.: US 11,103,155 B2
(45) Date of Patent: Aug. 31, 2021

(54) METHOD OF DETERMINING THE FREQUENCY OF A PERIODIC PHYSIOLOGICAL PROCESS OF A SUBJECT, AND A DEVICE AND SYSTEM FOR DETERMINING THE FREQUENCY OF A PERIODIC PHYSIOLOGICAL PROCESS OF A SUBJECT

(71) Applicant: Oxford University Innovation Limited, Oxford (GB)

(72) Inventors: David Andrew Clifton, Oxford (GB); Drew Birrenkott, Stanford, CA (US); Lionel Tarassenko, Oxford (GB); Marco Pimentel, London (GB)

(73) Assignee: Oxford University Innovation Limited, Oxford (GB)

( * ) Notice: Subject to any disclaimer, the term of this patent is extended or adjusted under 35 U.S.C. 154(b) by 375 days.

(21) Appl. No.: 16/179,729

(22) Filed: Nov. 2, 2018

(65) Prior Publication Data

US 2019/0069808 A1 Mar. 7, 2019

Related U.S. Application Data

(63) Continuation of application No. PCT/GB2017/051261, filed on May 5, 2017.

(30) Foreign Application Priority Data

May 10, 2016 (GB) ...................................... 1608170

(51) Int. Cl.
*A61B 5/08* (2006.01)
*A61B 5/024* (2006.01)
(Continued)

(52) U.S. Cl.
CPC ............ *A61B 5/0816* (2013.01); *A61B 5/024* (2013.01); *A61B 5/02416* (2013.01);
(Continued)

(58) Field of Classification Search
CPC ... A61B 5/0205; A61B 5/024; A61B 5/02405; A61B 5/02416–0255; A61B 5/0816;
(Continued)

(56) References Cited

U.S. PATENT DOCUMENTS

2007/0276265 A1   11/2007   Borgos
2009/0131803 A1*  5/2009    Heneghan ............ A61B 5/7264
                                                           600/484
(Continued)

FOREIGN PATENT DOCUMENTS

CN   101484069   7/2009
CN   102293637   12/2011

OTHER PUBLICATIONS

Addison et al. 'Secondary wavelet feature decoupling (swfd) and its use in detecting patient respiration from the photoplethysmogram.' In Engineering in Medicine and Biology Society, 2003. Proceedings of the 25th Annual International Conference of the IEEE, vol. 3, pp. 2602-2605. IEEE.

(Continued)

*Primary Examiner* — Thaddeus B Cox
(74) *Attorney, Agent, or Firm* — Levine Bagade Han LLP

(57) ABSTRACT

Methods, devices and systems for determining the frequency of a periodic physiological process of a subject, particularly respiration rate or heart rate, are disclosed. In one arrangement plural time windows of physiological data are obtained. Reference features corresponding to modulation modes are identified. Modulations of the reference features are extracted. Quality parameters are obtained by processing the extracted modulations. The quality parameters represent (Continued)

how strongly the extracted modulation exhibits a waveform of the periodic physiological process. The extracted modulations are processed to calculate the frequency of the periodic physiological process of the subject. The frequency of the periodic physiological process may be calculated using only a subset of the extracted modulations, the subset being selected using the quality parameter, or using a combination of the extracted modulations wherein each extracted modulation has a weighting defined by the quality parameter of the extracted modulation.

21 Claims, 8 Drawing Sheets

(51) Int. Cl.
  A61B 5/349    (2021.01)
  A61B 5/352    (2021.01)
  A61B 5/087    (2006.01)
  A61B 5/00     (2006.01)
(52) U.S. Cl.
  CPC ............ *A61B 5/087* (2013.01); *A61B 5/0809* (2013.01); *A61B 5/349* (2021.01); *A61B 5/352* (2021.01); *A61B 5/7225* (2013.01); *A61B 2562/0219* (2013.01)
(58) Field of Classification Search
  CPC .. A61B 5/349; A61B 5/352; A61B 2562/0219
  See application file for complete search history.

(56) References Cited

U.S. PATENT DOCUMENTS

| | | | |
|---|---|---|---|
| 2011/0291838 A1 | 12/2011 | Rantala | |
| 2013/0018239 A1* | 1/2013 | Lisogurski | A61B 5/7203 600/322 |
| 2014/0213861 A1* | 7/2014 | Van Leest | A61B 5/0075 600/323 |
| 2014/0228692 A1 | 8/2014 | Chan et al. | |
| 2015/0196257 A1* | 7/2015 | Yousefi | A61B 5/024 600/324 |
| 2016/0367198 A1* | 12/2016 | Chon | A61B 5/02416 |

OTHER PUBLICATIONS

Bing Nan Li et al. On an automatic delineator for arterial blood pressure waveforms. Biomedical Signal Processing and Control, 5(1):76-81, 2010.
Birrenkott. "Respiratory Qulaity Index Design and Validation for ECG and PPG Derived Respiratory Data", Trinity College University of Oxford, Dec. 11, 2015.
Cazares et al. Tracking poles with an autoregressive model: a confidence index for the analysis of the intrapartum cardiotocogram. Med Eng Phys, 23(9):603-14, 2001. Cazares, S Moulden, M Redman, W G Tarassenko, L Research Support, Non-U.S. Gov't Research Support, U.S. Gov't, Non-P.H.S. England Med Eng Phys. Nov. 2001;23(9):603-14.
Chan et al. "35th Annual International Conference of the IEE EMBS", published 2013, IEEE, pp. 4058-4061, Chan et al., "Ambulatory Respiratory Rate Detection Using ECG and a Triaxial Accelerometer".
Charlton et al. An Assessment of Algorithms for Estimation of Respiratory Rate from the Electrocardiogram and Photoplethysmogram Physiological Measurements 37, 2016, pp. 610-626.
Charlton et al. Breathing Rate Estimation from the Electrocardiogram and Photoplethysmogram: A Review IEEE Reviews in Biomedical Engineering 11, 2018, pp. 2-20.
Charlton et al. Extraction of Respiratory Signals from the Electrocardiogram and Photoplethysmogram: Technical and Physiological Determinants Physiological Measurement 38, 2017, pp. 669-690.
Chon et al. Estimation of respiratory rate from photoplethysmogram data using time-frequency spectral estimation. IEEE Trans Biomed Eng, 56(8):2054-63, 2009. 1558-2531. Chon, Ki H Dash, Shishir Ju, Kihwan Journal Article Research Support, U.S. Gov't, Non-P.H.S. United States IEEE Trans Biomed Eng. Aug. 2009;56(8):2054-63. doi: 10.1109/TBME.2009.2019766. Epub Apr. 14, 2009.
Clifton et al. "Bayesian Gaussian Processes for Identifying the Deteriorating Patient", PRS Transfer Report, Glen Wright Colopy, St. Cross College, University of Oxford, Sep. 6, 2015.
De Chazal et al, 'Automatic classification of sleep apnea epochs using the electrocardiogram.' In Computers in Cardiology 2000, pp. 745-748.
Duerichen et al. Multi-task Gaussian Processes for Multivariate Physiological Time-Series Analysis IEEE Transactions on Biomedical Engineering 62(1), 2015, pp. 314-322.
Garde et al. Estimating respiratory and heart rates from the correntropy spectral density of the photoplethysmogram. PLoS One, 9(1):e86427, 2014. 1932-6203 Garde, Ainara Karlen, Walter Ansermino, J Mark Dumont, Guy A Canadian Institutes of Health Research/ Canada Journal Article Research Support, Non-U.S. Gov't United States PLoS One. Jan. 22, 2014;9(1):e86427. doi:10.1371/journal. pone.0086427. eCollection 2014.
Hjorth. Electroencephalogr Clin Neurophysiol, 29(3):306-10, 1970. Hjorth, B Journal Article Netherlands Electroencephalogr Clin Neurophysiol. Sep. 1970;29(3):306-10.
Jarchi et al. Accelerometry-Based Estimation of Respiratory Rate for Post-Intensive Care Patient Monitoring IEEE Sensors 18(12), 2018, pp. 4981-4989.
Johnson et al.,"Computing in Cardiology 2013", published 2013, IEEE, pp. 791-794,"Improved Respiration Rate Estimation Using Kalman Filter and Wavelet Cross-Coherence".
Karlen et al. Multiparameter respiratory rate estimation from the photoplethysmogram. Biomedical Engineering, IEEE Transactions on, 60(7):1946-1953, 2013.
Karlen et al. Capnobase: Signal database and tools to collect, share and annotate respiratory signals. In Annual Meeting of the Society for Technology in Anesthesia (STA), West Palm Beach, p. 25. 2010.
Langley et al. Principal component analysis as a tool for analyzing beat-to-beat changes in ecg features: application to ecg-derived respiration. IEEE Trans Biomed Eng, 57(4):821-9, 2010. 1558-2531 Langley, Philip Bowers, Emma J Murray, Alan Journal Article Research Support, Non-U.S. Gov't United States IEEE Trans Biomed Eng. Apr. 2010;57(4):821-9. doi:10.1109/TBME.2009.2018297. Epub Apr. 7, 2009.
Lazaro et al: "Respiratory rate derived from smartphone-camera-acquired pulse photoplethysmographic signals", Physiological Measurement, Institute of Physics Publishing, Bristol, GB, vol. 26, No. 11, Oct. 9, 2015, pp. 2317-2333, XP020291312, ISSN: 0967-3334.
Li et al: "Robust heart rate estimation from multiple asynchronous noisy sources using signal quality indices and a Kalman filter; Robust heart rate estimation from multiple asynchronous noisy sources", Physiological Measurement, Institute of Physics Publishing, Bristol, GB, vol. 29, No. 1, Jan. 1, 2008, pp. 15-32, XP020130214, ISSN: 0967-3334.
Madhav et al. 'Estimation of respiratory rate from principal components of photoplethysmographic signals' In Biomedical Engineering and Sciences (IECBES), 2010 IEEE EMBS Conference on, pp. 311-314.
Meredith et al. Photoplethysmographic derivation of respiratory rate: a review of relevant physiology. Journal of medical engineering & technology, 36(1):1-7, 2012.
Morelli et al. Profiling the Propagation of Error from PPG to HRV Features in a Wearable Physiological-Monitoring Device IET Healthcare Technology Letters 5(2), 2018, pp. 59-64.
Nakajima et al. 'Photoplethysmographic measurement of heart and respiratory rates using digital filters.' In Engineering in Medicine and Biology Society, 1993. Proceedings of the 15th Annual International Conference of the IEEE, pp. 1006-1007.

(56) References Cited

OTHER PUBLICATIONS

Nemati et al: "Data Fusion for Improved Respiration Rate Estimation", Eurasip Journal on Applied Signal Processing, vol. 2010, No. 1, p. 926305, XP055282803, ISSN: 1687-6180.

Pimentel et al. Towards a Robust Estimation of Respiratory Rate from Pulse Oximeters IEEE Transactions on Biomedical Engineering 64(8), 2017, pp. 1914-1923.

Pimentel et al. Heart beat detection in multimodal physiological data using a hidden semi-markov model and signal quality indices. Physiol Meas, 36(8):1717-1727, 2015.

Saeed et al. Multiparameter intelligent monitoring in intensive care ii: a public-access intensive care unit database. Crit Care Med, 39(5):952-960, 2011.

Shah et al. Respiratory rate estimation during triage of children in hospitals. Journal of Medical Engineering & Technology, 39(8):514-524, 2015.

Shelley et al.. 'The use of joint time frequency analysis to quantify the effect of ventilation on the pulse oximeter waveform.' Journal of clinical monitoring and computing, 20(2):81-87, 2006.

Silva et al: "Signal Quality Estimation With Multichannel Adaptive Filtering in Intensive Care Settings", IEEE Transactions on Biomedical Engineering, IEEE Service Center, Piscataway, NJ, USA, vol. 59, No. 9, pp. 2467-2485, XP011490183, ISSN :0018-9294.

Takalo et al. Tutorial on univariate autoregressive spectral analysis. J Clin Monit Comput, 19(6):401-10, 2005. Takalo, Reijo Hytti, Heli Ihalainen, Heimo Journal Article Netherlands J Clin Monit Comput. Dec. 2005;19(6):401-10. Epub Jan. 25, 2006.

Yi et al. 'Derivation of respiration from ecg measured without subject's awareness using wavelet transform.' In Engineering in Medicine and Biology, 2002. 24th Annual Conference and the Annual Fall Meeting of the Biomedical Engineering Society EMBS/BMES Conference, 2002. Proceedings of the Second Joint, vol. 1, pp. 130-131 vol. 1.

Zhu et al. Bayesian Fusion of Physiological Measurements using a Signal Quality Extension Physiological Measurement 39(6), 2018, pp. 065008.

Zhu et al. Unsupervised Bayesian Inference to Fuse Biosignal Sensory Estimates for Personalising Care IEEE Journal of Biomedical and Health Informatics, 2018.

\* cited by examiner

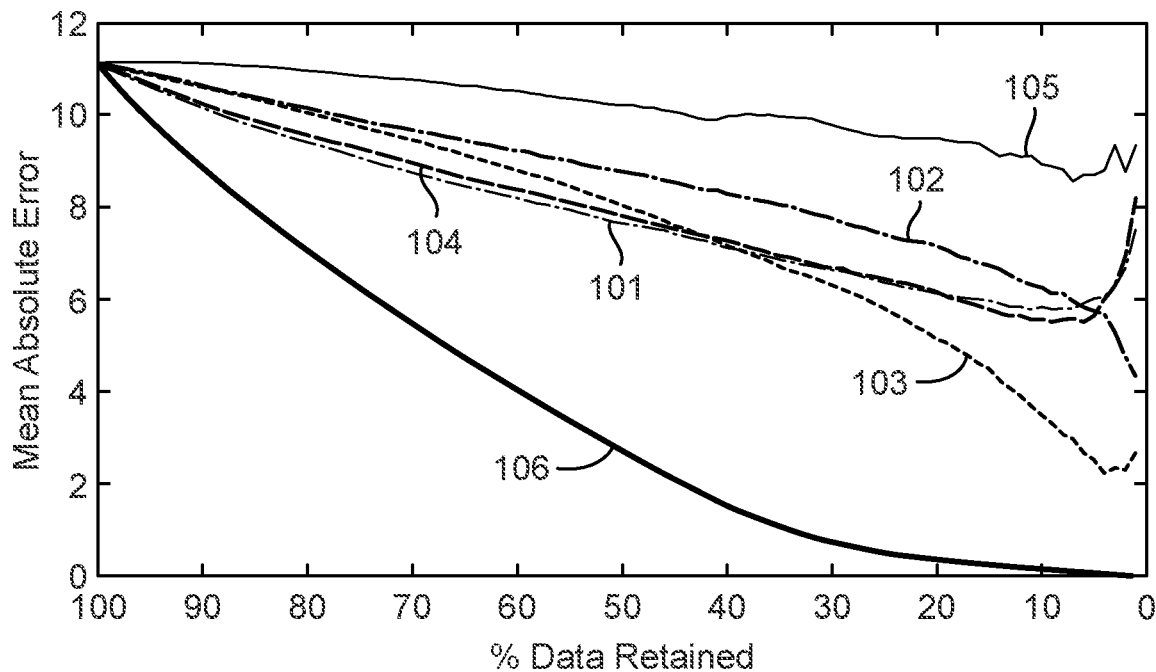
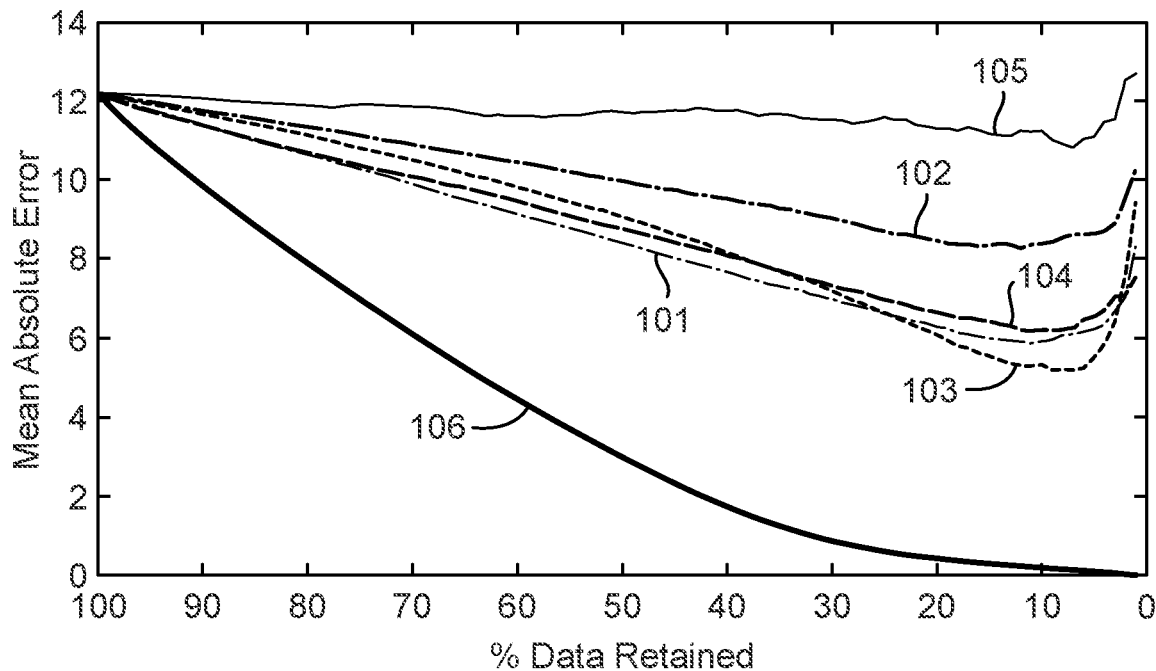

METHOD OF DETERMINING THE FREQUENCY OF A PERIODIC PHYSIOLOGICAL PROCESS OF A SUBJECT, AND A DEVICE AND SYSTEM FOR DETERMINING THE FREQUENCY OF A PERIODIC PHYSIOLOGICAL PROCESS OF A SUBJECT

CROSS-REFERENCE TO RELATED APPLICATIONS

This application continuation International Patent Application Number PCT/GB2017/051261 filed May 5, 2017, which claims priority to the GB Patent Application Number 1608170.5 filed May 10, 2016, the contents of which are incorporated herein by reference in their entirety.

BACKGROUND OF THE INVENTION

The present invention relates to measuring the frequency of a periodic physiological process, particularly respiration rate or heart rate.

While the clinical need for a technology that is capable of monitoring respiratory rate is apparent, there are currently few methods that are able to do this reliably, comfortably, and cost effectively. While a number of technologies, including spirometers, nasal thermocouples, transthoracic inductance, transthoracic impedance plethysmography, $CO_2$ capnography, and strain gauges, have all been used to monitor respiratory rate, they all require special equipment and may not be suitable for a general hospital setting. Of these, transthoracic impedance plethysmography (TTI) and $CO_2$ capnography are the most common clinically used methods; however, neither is ideal. TTI reliability is low due to electrode-skin impedance instabilities and skin irritation caused by the electrode gel. $CO_2$ capnography is invasive and diffcult to set up and use quickly.

In view of these challenges, for continuous monitoring of respiratory rate it would be desirable to extract respiratory rate from physiological signals that are already widely collected for patients throughout the hospital. While many different electronic monitoring technologies are used throughout the hospital, two of the most ubiquitous technologies are the electrocardiogram (ECG) and the photoplethysmography (PPG), which are used for collecting heart rate data and oxygen saturation ($SpO_2$, PPG only). In fact these technologies are so ubiquitous that it has been recommended that all patients on the general ward should be monitored either continuously or intermittently with, at a minimum, either ECG or PPG. The prevalence of both ECG and PPG in the hospital is of particular relevance as it has been widely shown that the heart rate and circulatory system rhythms are physiologically modulated by the respiratory rate via responses from both the nervous system and through physical alterations in the thoracic cavity caused by respiration.

While respiration has numerous modulations which allow it to be observed on the ECG—respiratory sinus arrhythmia (RSA), R-wave peak amplitude (RPA), and R-wave area (RWA)—and PPG—respiratory-induced amplitude variation RIAV), respiratory-induced intensity variation (RIIV), and respiratory-induced frequency variation (RIFV)—actually extracting these measures and obtaining a medically useful respiratory rate is more difficult. Many different methods have been used to try to extract one or more of these modulations from the ECG and PPG including: digital filters, short-time fast Fourier transform, wavelet decomposition, autoregression, time-frequency spectral estimation, principle component analysis, and correntropy spectral density. This known methods are described briefly below.

Digital Filters

One of the simplest methods for obtaining the respiratory rate, particularly and most often the RIIV from the PPG, has been digital filtering. This is because the RIIV represents a unique respiratory signal in the DC region of the PPG while the cardiac signal lies in the AC region. As a result, it has been possible to extract both the cardiac signal and the RIIV signal from the PPG by using different digital filters to remove the desired signal from the noise. In one of the first instances of using digital filtering to detect respiratory rate from PPG, it was found that it was possible to extract the cardiac signal using a bandpass filter and then based on the estimated heart rate, one of three low-pass filters with varying cut-off frequencies could be used to detect the respiratory signal. Most often methods using digital filters have extracted the respiratory signal from the PPG using either the fast Fourier transform or simple peak detection. Through time-series analysis techniques, digital filters have been used to extract respiratory rate from the RIAV, RIIV, and RIFV modulations of the PPG and the RSA from the ECG. See, for example, K. Nakajima, T. Tamura, T. Ohta, H. Miike, and P. A. Oberg. Photoplethysmographic measurement of heart and respiratory rates using digital filters. In Engineering in Medicine and Biology Society, 1993. Proceedings of the 15th Annual International Conference of the IEEE, pages 1006-1007, and P. de Chazal, C. Heneghan, E. Sheridan, R. Reilly, P. Nolan, and M. O'Malley. Automatic classification of sleep apnea epochs using the electrocardiogram. In Computers in Cardiology 2000, pages 745-748.

Short-Time Fast Fourier Transform (STFFT)

In addition to simple digital filtering methods, the STFFT has been used to estimate respiratory rate of the RIIV signal in the PPG. One of the limitations of the FFT is that it can only detect if a certain frequency is present in a sample of data, it cannot detect where that frequency is present in the signal. The STFFT, in contrast, uses much smaller sliding windows and performs sequential FFTs on those windows. This allows for a much finer time resolution as well as the observation of long term trends when all of the data are plotted and viewed together. See, for example, Kirk H Shelley, Aymen A Awad, Robert G Stout, and David G Silverman. The use of joint time frequency analysis to quantify the effect of ventilation on the pulse oximeter waveform. Journal of clinical monitoring and computing, 20(2):81-87, 2006.

Wavelet Decomposition

Both the continuous wavelet decomposition and the discrete wavelet decomposition have been used to extract the respiratory rate from the ECG and PPG. Wavelet decomposition has been widely used in signal processing as it allows the time-frequency unfolding of signals in the time domain. The wavelet decomposition method works by cross-correlating the input signal with a wavelet function of a given length and shifting that function the entire length of the input signal. The wavelet function is then stretched and the process is repeated. This is done repeatedly and ultimately allows for a finer understanding of the details of a signal to emerge which is particularly useful when dealing with signals where the long-term frequency is not necessarily uniform (i.e. the respiratory rate over a long period of time will not remain the same). See, for example, W. J. Yi and K. S. Park. Derivation of respiration from ecg measured without subject's awareness using wavelet transform. In Engineering in Medicine and Biology, 2002. 24th Annual Conference and the Annual Fall Meeting of the Biomedical Engineering Society EMBS/BMES Conference, 2002. Proceedings of the Second Joint, volume 1, pages 130-131 vol. 1, and PS Addison and JN Watson. Secondary wavelet feature decoupling (swfd) and its use in detecting patient respiration from the photoplethysmogram. In Engineering in Medicine and Biology Society, 2003. Proceedings of the 25th Annual International Conference of the IEEE, volume 3, pages 2602-2605. IEEE.

Autoregression

Autoregressive modelling works on the principle of using a certain number of previous data points to explain the current data point. In essence, it is a linear prediction where the current value is modelled as a sum of a set number (p) of the preceding values. The result of an autoregressive model is a number of poles which represent the dominant frequencies in a signal. Using this information, and with proper pre-processing, the highest magnitude poles (the poles that are most dominant in the signal) can be used to express the respiratory rate. A simple autoregressive model has been used to extract RIIV information from the PPG and the RSA and RPA from the ECG. Furthermore, more computationally advanced methods have used autoregression as the core of their respiratory rate estimation algorithms including ARxCor and ARSpec. See, for example, D. Clifton, M. A. F. Pimentel, A. E. W. Johnson, P. Charlton, S. A. Shah, A. Guazzi, and L. Tarassenko. Estimation of respiratory rate from pulse oximeters, 2015, and Syed Ahmar Shah, Susannah Fleming, Matthew Thompson, and Lionel Tarassenko. Respiratory rate estimation during triage of children in hospitals. *Journal of Medical Engineering & Technology*, 39(8):514-524, 2015).

Time-Frequency Spectral Estimation

Time-frequency spectral estimation, specifically variable-frequency complex demodulation (VFCDM) has been used to extract the RIIV signal from the PPG. VFCDM is a two-step process. The first step is to decompose the signal into sinusoidal modulations using complex demodulation. The second step is to use the calculated centre frequencies from the previous step as the backbone to obtain the entire frequency spectrum. See, for example, K. H. Chon, S. Dash, and K. Ju. Estimation of respiratory rate from photoplethysmogram data using time-frequency spectral estimation. IEEE Trans Biomed Eng, 56(8):2054-63, 2009. 1558-2531 Chon, Ki H Dash, Shishir Ju, Kihwan Journal Article Research Support, U.S. Gov't, Non-P.H.S. United States IEEE Trans Biomed Eng. 2009 August; 56(8):2054-63. doi: 10.1109/TBME.2009.2019766. Epub 2009 Apr. 14.

Principal Component Analysis (PCA)

PCA is method that is most often used for identifying patterns in data and reducing the dimensionality of large, multidimensional data sets. However, by separating individual heartbeats from either the PPG or ECG, it is possible to obtain a feature matrix which contains all the individual heartbeats in which PCA can be conducted. By doing this, the dimensionality of the heartbeats is reduced and the principle component (PC), the axis that contains most of the variation, can be extracted. This technique has been used successfully to extract the RIIV and RIFV from the PPG and the RPA and RWA from the ECG. See, for example, K. V. Madhav, M. R. Ram, E. H. Krishna, K. N. Reddy, and K. A. Reddy. Estimation of respiratory rate from principal components of photoplethysmographic signals. In Biomedical Engineering and Sciences (IECBES), 2010 IEEE EMBS Conference on, pages 311-314, and P. Langley, E. J. Bowers, and A. Murray. Principal component analysis as a tool for analyzing beat-to-beat changes in ecg features: application to ecg-derived respiration. IEEE Trans Biomed Eng, 57(4): 821-9, 2010. 1558-2531 Langley, Philip Bowers, Emma J Murray, Alan Journal Article Research Support, Non-U.S. Gov't United States IEEE Trans Biomed Eng. 2010 April; 57(4):821-9. doi:10.1109/TBME.2009.2018297. Epub 2009 Apr. 7.

Correntropy Spectral Density (CSD)

CSD is one of the most recent techniques used for extracting the respiratory rate. CSD provides improved resolution in the frequency spectrum compared to standard power spectral density methods. The method works using correntropy, a correlation function that can provide information on higher-order statistics. The method has recently been used to predict the heart and respiratory rates from PPG data. See, for example, A. Garde, W. Karlen, J. M. Ansermino, and G. A. Dumont. Estimating respiratory and heart rates from the correntropy spectral density of the photoplethysmogram. PLoS One, 9(1):e86427, 2014. 1932-6203 Garde, Ainara Karlen, Walter Ansermino, J Mark Dumont, Guy A Canadian Institutes of Health Research/Canada Journal Article Research Support, Non-U.S. Gov't United States PLoS One. 2014 Jan. 22; 9(1):e86427. doi:10.1371/journal.pone.0086427. eCollection 2014.

Currently, the process of detecting the respiratory rate from either the PPG or ECG is a four step process. The first step is the acquisition of the data from the PPG or ECG monitor. The second step is an optional step that looks to discard poor quality data due to a variety of factors including: detached leads, low signal to noise ratio, and poor lead placement among others. Many algorithms for both PPG and ECG have been derived to achieve this aim. The third step is extracting the relevant time series features based on the previously described modulations of the respiratory rate on the ECG and PPG. The fourth step is applying one of the suites of respiratory rate detection algorithms mentioned above. Of note is the fact that some of these detection algorithms are designed to work for specific respiratory modulations (i.e. RIIV) and as a result feature extraction is not necessary for these methods; however, many of these methods can be adapted for all six of the noted respiratory modulations if a feature extraction step is first implemented. This methodology for extracting the respiratory rate however has a number of shortcomings related to the quality of the respiratory signals that can be obtained for any one of the modulations described. Particularly, the modulations are often very subtle and even under ideal circumstances are hard to detect. Furthermore, for clinical populations, ideal circumstances are nearly impossible to achieve and often the signals are corrupted with noise artefacts. To compound these challenges, it has been widely found that the specific respiratory modulations on the ECG and PPG are patient specific and it is hard to predict which modulation will be most prevalent for a particular patient. For example one study found that the PPG modulations that worked best for patients was dependent on a multitude of factors including gender, body position, and respiratory rate. Further research on RSA as a physiological phenomenon has shown that its prevalence is highly dependent on pre-existing health conditions, age, hydration levels, and a patient's level of physical activity. In addition to being patient-specific, modulations can also vary within one patient's recordings, for example appearing and disappearing with time, varying health status, etc.

Ultimately, these shortcomings suggest that for any respiratory rate extraction algorithm used on its own, even the best-performing or most-sophisticated algorithm, extraction of the respiratory rate from the PPG or ECG for all patients may not be possible. This shortcoming has led researchers to try to account for this by pursuing multi-parameter and smart fusion methods that are capable of taking respiratory rate estimations from multiple different modulations and merging them into a single respiratory rate.

Corresponding challenges exist when measuring other periodic physiological processes, such as heart rate.

BRIEF SUMMARY OF THE INVENTION

It is an object of the invention to provide improved methods and apparatus for measuring the frequency of a periodic physiological process such as respiration rate or heart rate.

According to an aspect of the invention, there is provided a method of determining the frequency of a periodic physiological process of a subject, comprising: obtaining plural time windows of data representing physiological measurements on the subject; identifying reference features corresponding to one or more modulation modes of the physiological measurements in each of the time windows; for each modulation mode, extracting a modulation of the corresponding reference features in each time window; processing each extracted modulation to obtain a quality parameter for each combination of modulation mode and time window, the quality parameter representing how strongly the extracted modulation exhibits a waveform of the periodic physiological process; and processing the extracted modulations to calculate the frequency of the periodic physiological process of the subject, wherein: the frequency of the periodic physiological process is calculated using only a subset of the extracted modulations, the subset being selected using the quality parameters, the frequency of the periodic physiological process is calculated using a combination of the extracted modulations, each extracted modulation having a weighting defined by the quality parameter of the extracted modulation, or the frequency of the periodic physiological process is calculated using only a subset of the extracted modulations, the subset being selected using the quality parameters, and the frequency of the periodic physiological process is calculated using a combination of the selected subset of extracted modulations, each one of the selected subset of extracted modulations having a weighting defined by the quality parameter of the extracted modulation.

The inventors have found that by obtaining a quantitative measure of data quality (quality parameter) after the extraction of modulations from the physiological data (e.g. ECG or PPG), the input for subsequent processing to calculate the frequency of the periodic physiological process (e.g. respiration rate or heart rate) can be significantly improved. An increase in the stability and/or accuracy of the frequency of the periodic physiological process output can be obtained. Alternatively or additionally, the processing power needed to achieve a given level of stability or accuracy can be reduced. The quality parameter may be used, for example, to filter data prior to input to steps to calculate the frequency of the periodic physiological process (e.g. by selecting time windows and/or modulation modes using the quality parameter). Alternatively or additionally, the quality parameter may be used to apply weightings in the calculating steps which reflect a relative confidence in information extracted from particular time windows and/or modulation modes.

The inventors have demonstrated that this approach can more accurately classify respiratory signals as being of high or low quality than a signal quality index applied prior to extracting modulations of reference features in the physiological data. The inventors have further demonstrated that the quality parameters can work effectively on multiple datasets of varying signal quality.

It has been found particularly effective to obtain the quality parameter by Fourier transforming the extracted modulation and evaluating a property of the largest peak in the Fourier transform with respect to the properties of the spectrum of the signal within the range of frequencies of interest. The range of frequencies of interest can be defined for example to be the group of physiologically plausible values of the frequency of the periodic physiological process (e.g. respiration rate or heart rate).

It has also been found to be particularly effective to obtain the quality parameter by evaluating a root of the polynomial in the denominator of the transfer function for an autoregressive model representing a dominant frequency component in the extracted modulation.

It has also been found to be particularly effective to obtain the quality parameter by evaluating a maximum autocorrelation between copies of the extracted modulation in the time window that are shifted in time relative to each other.

It has also been found to be particularly effective to obtain the quality parameter by evaluating the Hjorth complexity.

It has also be found to be particularly effective to obtain a quality parameter using a combination of one or more of 1) transforming the extracted modulation and evaluating a property of the largest peak in the Fourier transform with respect to the properties of the entire frequency spectrum of the signal; 2) evaluating a root of the polynomial in the denominator of the transfer function for an autoregressive model representing a dominant frequency component in the extracted modulation; 3) evaluating a maximum autocorrelation between copies of the extracted modulation in the time window that are shifted in time relative to each other; and 4) evaluating the Hjorth complexity.

According to an alternative aspect, there is provided a device for determining the frequency of a periodic physiological process of a subject, comprising: a data receiving unit configured to receive plural time windows of data representing physiological measurements on the subject; a data processing unit configured to: identify reference features corresponding to one or more modulation modes of the physiological measurements in each of the time windows; for each modulation mode, extract a modulation of the corresponding reference features in each time window; process each extracted modulation to obtain a quality parameter for each combination of modulation mode and time window, the quality parameter representing how strongly the extracted modulation exhibits a waveform of the periodic physiological process; and process the extracted modulations to calculate the frequency of the periodic physiological process of the subject, wherein: the frequency of the periodic physiological process is calculated using only a subset of the extracted modulations, the subset being selected using the quality parameters, the frequency of the periodic physiological process is calculated using a combination of the extracted modulations, each extracted modulation having a weighting defined by the quality parameter of the extracted modulation, or the frequency of the periodic physiological process is calculated using only a subset of the extracted modulations, the subset being selected using the quality parameters, and the frequency of the periodic physiological process is calculated using a combination of the selected subset of extracted modulations, each one of the selected subset of extracted modulations having a weighting defined by the quality parameter of the extracted modulation.

According to an alternative aspect, there is provided a system for determining the frequency of a periodic physiological process of a subject comprising a device for measuring the respiration rate of a subject according to an embodiment and a data processing station connectable to the device via a network, wherein the system is configured to distribute processing of the extracted modulations to extract the frequency of a periodic physiological process of the subject between the device and the data processing station according to the quality measures of the extracted modulations determined by the device.

The quality parameters can thereby be used to distribute processing intelligently between a device which is in close proximity to the subject (and which may be a portable or low power device, for example), and a processing station which can be remote from the subject (and therefore of higher power or processing capacity). A desirable balance between minimising data traffic between the device and the processing station and accuracy of the determined frequency provided at the device can be achieved.

BRIEF DESCRIPTION OF THE SEVERAL VIEWS OF THE DRAWINGS

The invention will be further described by way of example with reference to the accompanying drawings.

FIG. 7 is a plot showing performance of RQIs and SQI on a MIMIC II dataset using PPG data and using the ARSpec estimation algorithm to determine the absolute difference of the respiration rate estimation from the standard. Performance is displayed as the mean absolute error (MAE) values for each quality parameter (RQI) as the poorest quality data is sequentially removed.

FIG. 8 is a plot showing performance of RQIs and SQI on the MIMIC II dataset using ECG data and using the ARSpec estimation algorithm to determine the absolute difference of the respiration rate estimation from the standard. Performance is displayed as the mean absolute error (MAE) values for each quality parameter (RQI) as the poorest quality data is sequentially removed.

DETAILED DESCRIPTION OF THE INVENTION

In the following, references to a subject are to be understood as references to any biological organism to which a frequency of a periodic physiological process is applicable. The periodic physiological process may be respiration rate (i.e. rate of breathing) or heart rate. The subject will typically be a human, but could also be an animal.

References to physiological measurements are to be understood to encompass any measurement of a physiological property of the subject which is capable of containing information about the periodic physiological process of interest. As described below, embodiments of the invention are particularly applicable to electrocardiogram measurements, which will be referred to as ECG, and photoplethysmography measurements, which will be referred to as PPG, and to respiration rate as the frequency of the periodic physiological process. Embodiments of the invention are also applicable to accelerometer measurements (which measure patient movement). The accelerometer measurements may be implemented using a triaxial accelerometer. Such accelerometers are routinely incorporated into consumer electronic devices.

References to time windows of data are to be understood to comprise data taken at different times, for example as a time series, during a particular period of time (time window). The data may comprise time series data.

Any of the steps described below may be performed using a suitably programmed computer. A computer program or computer program product comprising the computer program may provide code to instruct the computer to perform the steps.

Figure 9:
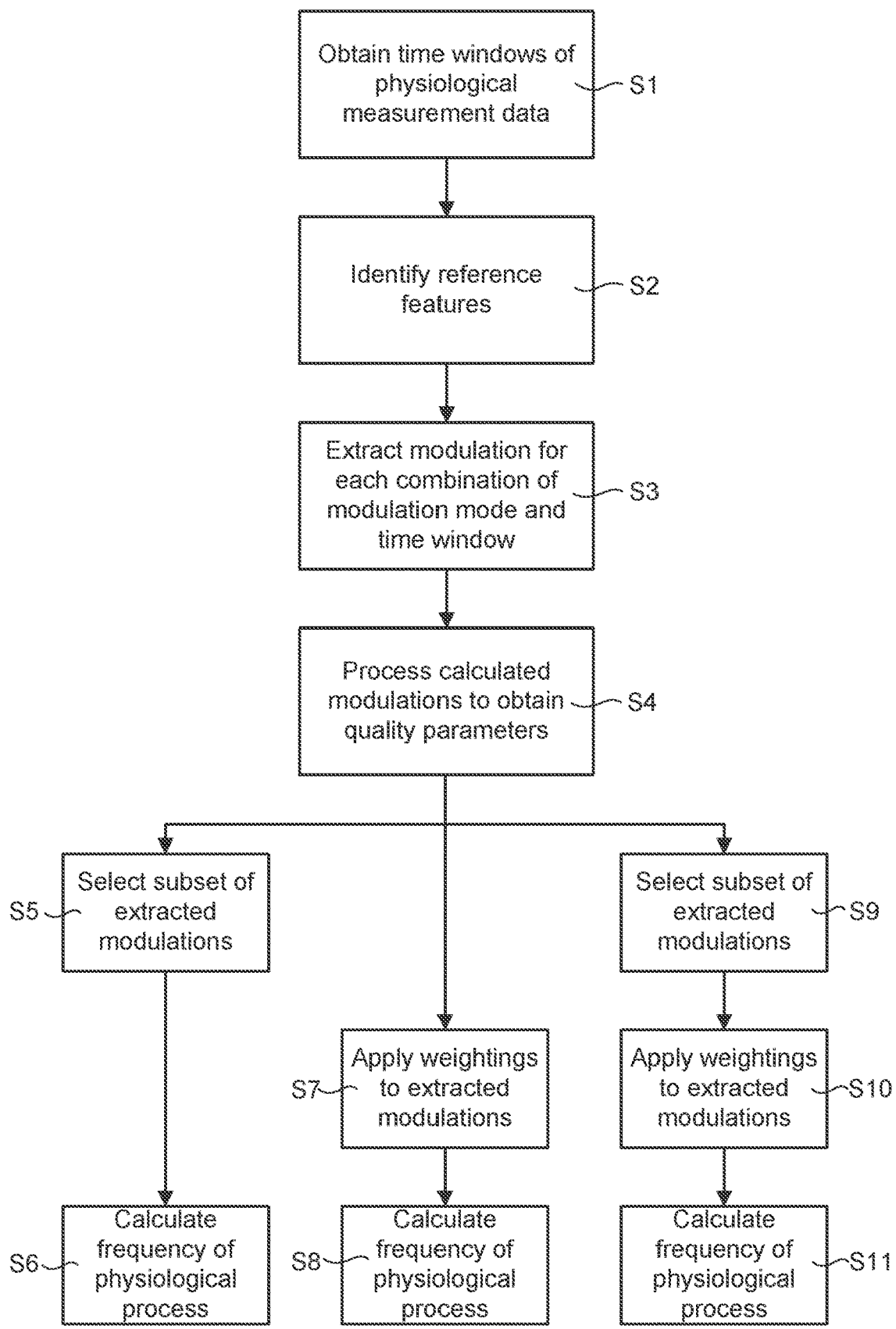
FIG. 9 depicts a method of determining the frequency of the physiological process according to an embodiment.
Figure 10:
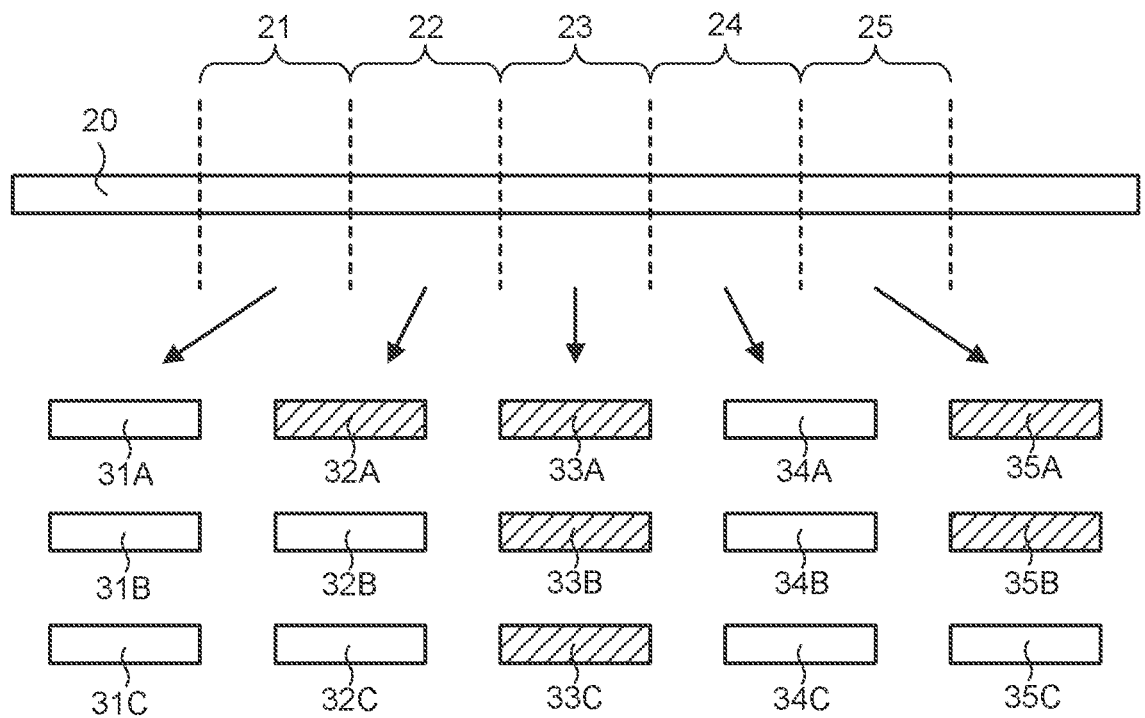
FIG. 10 illustrates obtaining time windows of data, extracting modulations for different combinations of time window and modulation mode, and selecting of a subset of the extracted modulations.
Figure 11:
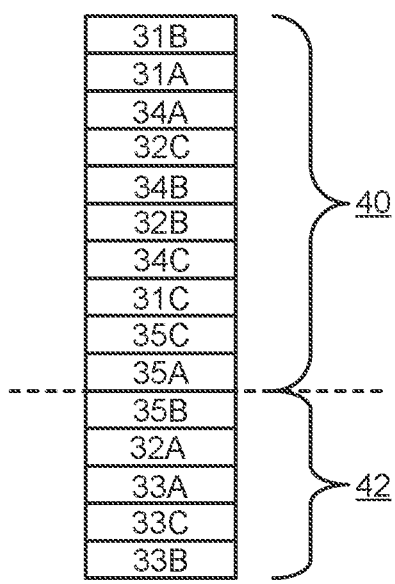
FIG. 11 illustrates selecting of a subset of extracted modulations according to an embodiment.
Figure 12:
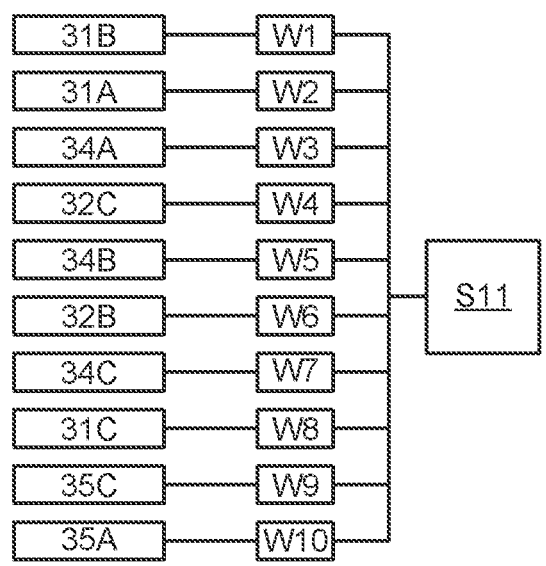
FIG. 12 depicts applying of weightings to a selected subset of extracted modulations.

FIG. 9 depicts steps of a method of determining the frequency of a periodic physiological process of a subject according to an embodiment. FIGS. 10 to 12 illustrate example stages of the method.

In step S1, a plurality of time windows of data 21-25 are obtained. As depicted schematically in FIG. 10, the time windows 21-25 may be extracted by windowing a stream of data 20. In a detailed example described below, an eight minute waveform segment is described as an example of the stream of data 20 and 15 unique, non-overlapping 32 second time windows of data are extracted from the eight minute waveform segment. In other embodiments the time windows may overlap with each other.

Each of the time windows 21-25 contains data representing physiological measurements that have been made on a subject, for example as a time series of data points which each represent a measurement made at a different time within the time window 21-25. The method may include performing the physiological measurements or the time windows of data may be obtained from measurements made at a previous time, for example from a storage medium or over a network.

In step S2, reference features corresponding to one or more modulation modes of the physiological measurements are identified in each of the time windows 21-25. The reference features are identifiable properties of the raw physiological measurements which can be used as references to identify modulation of the physiological measurements by the periodic physiological process of interest (e.g. respiration rate). As described below, there are various mechanisms by which respiration rate can influence physiological measurements such as ECG and PPG. Different modulation modes may correspond to different mechanisms or different combinations of mechanisms. The strength of modulation in any given modulation mode may vary according to the particular clinical situation and patient, and/or may vary with time, due to the different mechanisms involved. As described in further detail below, in the case where the physiological measurements comprise ECG measurements, the reference features may comprise one or more of the following: Q-wave minimum and R-wave maximum. The modulation modes for ECG may comprise one or more of the following: respiratory sinus arrhythmia (RSA), R-wave peak amplitude (RPA), and R-wave area (RWA). In the case where the physiological measurements comprise PPG measurements, the reference features may comprise one or more of the following: peaks of the PPG measurements and troughs of the PPG measurements. The modulation modes for PPG may comprise one or more of the following: respiratory-induced amplitude variation (RIAV), respiratory-induced intensity variation (RIIV), and respiratory-induced frequency variation (RIFV).

Further details about pulmonary modulation of the cardiac system and about the origins of observable modulations of the respiratory system in ECG and PPG waveforms are given below in the sections headed "Pulmonary Modulation of the Cardiac System" and "Observable Modulations of Respiratory System in ECG and PPG Waveforms".

In step S3, modulation of the reference features for each of the one or more modulation modes (e.g. one or more of RSA, RPA, RWA, RIAV, RIIV, and RIFV) is extracted in each of the time windows. Thus, an extracted modulation is obtained for each combination of modulation mode and time window. This is illustrated schematically in the lower part of FIG. 10. Here, boxes 31A-C represent extracted modulations for time window 21. Box 31A represents an extracted modulation for a first modulation mode, box 31B represents an extracted modulation for a second modulation mode, and box 31C represents an extracted modulation for a third modulation mode. Boxes 32A-C, 33A-C, 34A-C, and 35A-C respectively represent corresponding extracted modulations for the time windows 22-25. Five time windows with three modulation modes each are used here only as an illustrative example. Fewer or more time windows and fewer or more modulation modes may be used.

In step S4, the extracted modulations obtained in S3 are processed to obtain a quality parameter for each combination of modulation mode and time window. Thus, in the example of FIG. 10, a distinct quality parameter is obtained for each of the 15 boxes shown in the lower part of the figure. The quality parameter may be referred to as a respiratory quality index (RQI). The quality parameter comprises a value representing how strongly the extracted modulation exhibits a waveform of the periodic physiological process (e.g. respiratory rate). Thus, for example, where the respiratory rate waveform is relatively strongly modulated onto the extracted modulation the quality parameter may comprise a high value and when the respiratory rate waveform is relatively weakly modulated onto the extracted modulation the quality parameter may comprise a lower value. The quality parameter can be defined in various ways, however, including in such a way that there is an inverse correlation with the strength of the modulation.

The next series of steps comprise processing of the extracted modulations to calculate the frequency of the periodic physiological process of the subject. This can be done in various ways. In one embodiment, steps S5 and S6 are performed in sequence. In an alternative embodiment steps S7 and S8 are performed in sequence. In a further alternative embodiment steps S9-S11 are performed in sequence.

In the sequence starting with step S5, a subset of the extracted modulations is selected using the quality parameters. The subset may comprise for example only those extracted modulations in which the strength of the waveform of the periodic physiological process (e.g. respiratory waveform) is above a predetermined level, by comparing the quality parameters with a corresponding predetermined threshold value. Thus, where the quality parameter is defined such that there is a positive correlation between the strength of the waveform of the periodic physiological process in the extracted modulation and the quality parameter, the selected subset of extracted modulations may comprise all those extracted modulations which have a quality parameter above the predetermined threshold value. The result of a process of this type is illustrated schematically in the lower part of FIG. 10, wherein the non-hatched boxes represent extracted modulations which have been selected (i.e. which are part of the selected subset) and the hatched boxes represent extracted modulations which have been rejected. In this example it can be seen that time windows 21 and 24 yield two sets of three extracted modulations with relatively favourable quality parameters, possibly indicating time periods during which conditions for physiological measurements were relatively favourable (e.g. when the subject was stationary). Time window 23 yields three extracted modulations which are all of poor quality, possibly indicating less favourable measurement conditions. Time windows 22 and 25 illustrate a mixed case where some of the modulation modes yield high quality data and some yield lower quality data.

FIG. 11 illustrates an alternative approach for selecting the subset of extracted modulations using the quality parameters. In this embodiment, the selecting of the subset of the extracted modulations is performed by selecting a predetermined proportion of the extracted modulations in descending order of the strength of the waveform of the periodic physiological process, as represented by the quality parameters. In the present example, the extracted modulations represented by the 15 boxes in FIG. 10 have been ordered from top to bottom in descending order of the strength of the waveform. The predetermined proportion in this case is two thirds, so the top ten extracted modulations 40 form the selected subset. The remaining extracted modulations 42 are rejected.

The selected subset of extracted modulations are used to extract the frequency of the periodic physiological process in step S6 while the non-selected extracted modulations are not used.

In the sequence starting with the step S7, a weighting is applied to each extracted modulation according to the quality parameter of the extracted modulation. The frequency of the periodic physiological process is then extracted (step S8) using a combination of the weighted extracted modulations. Extracted modulations which exhibit the waveform of the periodic physiological process only relatively weakly are weighted less strongly (and are therefore made to contribute less to the final calculated frequency) than modulations which exhibit the waveform of the periodic physiological process more strongly. Methods for combining different data using weightings are well known in the art. The weightings could be obtained via linear regression, or they could be adaptive, and learned for individual patients, using other regression-based methods.

In the sequence starting with step S9, processes corresponding to both of steps S5 and S7 are performed. The approach is illustrated schematically in FIG. 12. In step S9, a subset of the extracted modulations is selected using the quality parameters (as in S5). The resulting subset of modulations is shown in the left-hand column of boxes (extracted modulations) in FIG. 12. In step S10, weightings are applied (depicted by W1-W10 in FIG. 12) to each of the selected subset of extracted modulations (similar to step S7). In step S11, the frequency of the periodic physiological process is calculated using a combination of the selected subset of extracted modulations, each weighted according to its quality parameter.

Various standard techniques may be used in the steps for calculating the frequency of the periodic physiological process from the selected subset of extracted modulations and/or weighted extracted modulations in step S6, S8 or S11. For example one or more of the following techniques described in the introductory part of the description may be used: Digital Filters, Short-Time Fast Fourier Transform, Wavelet Decomposition, Autoregression, Time-Frequency Spectral Estimation, Principal Component Analysis, or Correntropy Spectral Density. Thus, given the quality parameter, it is possible to go on to obtain the frequency of the periodic physiological process in the usual manner, safe in the knowledge that the input data are of sufficient quality to make the result reliable.

As illustrated in the examples shown in FIGS. 10-12, the applying of weightings may comprise applying different weightings to extracted modulations corresponding to different modulation modes in the same time window of data, different weightings to extracted modulations in different time windows, or both.

Figure 13:
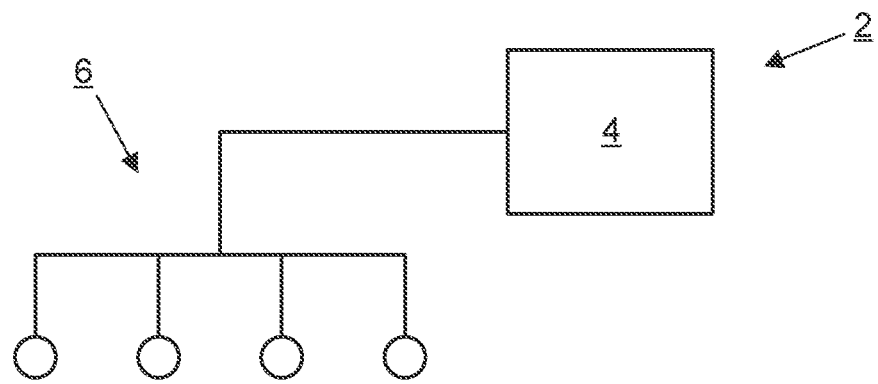
FIG. 13 is a schematic side view of a device for determining the frequency of a periodic physiological process.

FIG. 13 depicts an example of a device 2 for determining the frequency of a periodic physiological process of a subject. The device 2 comprises a processing unit 4 which performs the method of determining the frequency of the periodic physiological process according to any embodiment. Optionally, the device 2 comprises a sensing system 6 which performs physiological measurements on the subject (e.g. ECG or PPG). The device 2 may also comprise a data receiving unit for receiving the plural time windows of data representing the physiological measurements on the subject.

Figure 14:
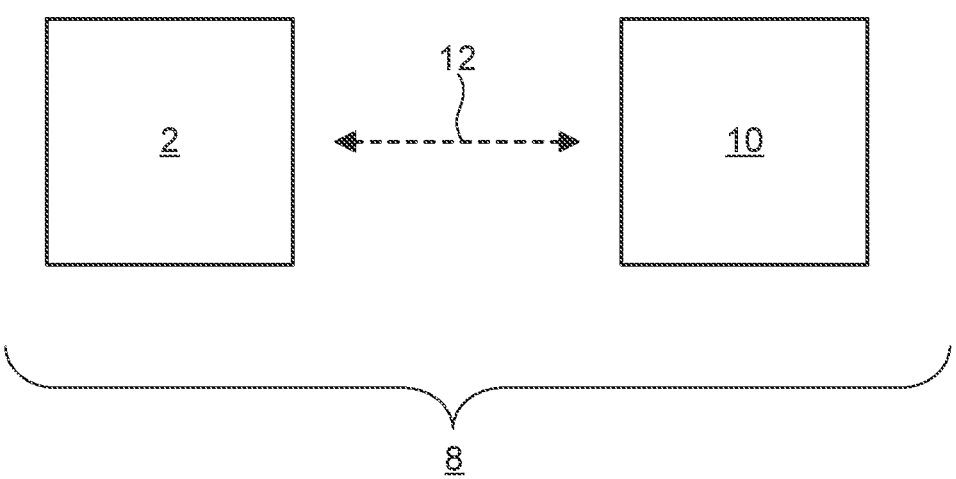
FIG. 14 depicts a system for determining the frequency of a periodic physiological process.

FIG. 14 depicts a system 8 for determining the frequency of a periodic physiological process of a subject. The system 8 comprises a device 2 for determining the frequency of the periodic physiological process of the subject according to an embodiment. The system 8 further comprises a data processing station 10 connectable via a network 12 (wired or wireless) to the device 2. The system 8 is configured to distribute processing of the extracted modulations to calculate the frequency of the periodic physiological process between the device 2 and the data processing station 10 according to the quality parameters of the extracted modulations obtained by the device. For example, in an embodiment the device 2 is configured such that for extracted modulations having a quality parameter indicating that the strength of the waveform of the periodic physiological process is higher than a first predetermined level, the device 2 extracts the frequency itself, whereas for at least a portion of the extracted modulations having a quality parameter indicating that the strength of the waveform of the periodic physiological process is lower than the first predetermined level, the device 2 sends the extracted modulations to the data processing station 10 for processing, where more computing resources may be available to process these more difficult time windows. In this way more difficult processing is performed by the higher power data processing station 10 rather than the device 2. Alternatively or additionally, the device 2 may be configured such that for extracted modulations having a quality parameter indicating that the strength of the waveform of the periodic physiological process is higher than a second predetermined level, the device 2 sends the extracted modulations to the data processing station 10 for processing, whereas for at least a portion of the extracted modulations having a quality parameter indicating that the strength of the waveform of the periodic physiological process is lower than the second predetermined level, the device 2 processes the extracted modulations itself or discards the extracted modulations. In this way, bandwidth between the device 2 and the processing station 10, and/or processing power of the processing station 10, is not wasted on extracted modulations of lower quality.

Details about how the quality parameters may be derived in different embodiments of the invention are provided below.

Fourier Transform RQI

In an embodiment the obtaining of the quality parameter for each extracted modulation in each time window comprises Fourier transforming the extracted modulation in the time window and evaluating a property of the largest peak in the Fourier transform.

The Fourier transform is a signal processing method used to describe the harmonic or frequency content within a time-series based waveform. Where x(n) is a discrete time-signal, the discrete Fourier transform (DFT) can be defined as:

$$X(m) = \sum_{n=0}^{N-1} x(n)e^{-j2\pi nm/N}$$

where X(m) represents the output of the time-series waveform x(n) in the frequency domain. However, in most discrete signal processing based algorithms, the discrete Fourier transform is replaced by the equivalent fast-Fourier transform (FFT) due to its increased processing speed. When the quality parameter is generated using an FFT it is referred to herein as the $RQI_{FFT}$.

In an embodiment, the $RQI_{FFT}$ is calculated by first conducting $RQI_{FFT}$ specific pre-processing on x(n), where x(n) specifically represents an extracted modulation for one time window of data (e.g. a 32 second window) for one patient for one of the specific modulations (ECG: RSA, RPA, RWA, PPG: RIAV, RIIV, RIFV). Specifically, prior to taking the FFT of x(n), x(n) is zero-padded, where necessary, linearly detrended, and windowed using a Hamming window function. After pre-processing, the FFT of x(n) is taken yielding X(m). X(m) is used to calculate the maximum peak area (MPA) of the FFT which is calculated as the sum of an integer number of largest continuous values of X(m) in the region of the largest value of X(m) within the frequency spectrum of interest from a lower frequency limit (e.g. 0.1 Hz, which corresponds to 6 breaths/min) to an upper frequency limit (e.g. 0.75 Hz, which corresponds to 45 breaths/min, or 1 Hz). For example, the MPA could be represented by one of the following sums where M represents the index of the largest value of X(m):

$$MPA = X(M-2) + \ldots + X(M)$$

$$MPA = X(M-1) + \ldots + X(M+1)$$

$$MPA = X(M) + \ldots + X(M+2)$$

Following the calculation of the MPA, the total area of the FFT within the physiological range of interest (e.g. respiratory range), termed total respiratory area (TRA) in the case of respiration rate, is calculated as the sum of all values X(m) that fall between the frequency range (e.g. 0.1 Hz to 0.75 Hz or 0.1 Hz to 1. Hz). Using these two values, the $RQI_{FFT}$ is calculated as:

$$RQI_{FFT} = MPA/TRA$$

An alternative expression is given below:

$$RQI_{FFT} = \frac{\sum_{i=1}^{n} X(m_i)}{\sum_{m=fmin}^{fmax} X(m)}$$

where $$\sum_{m=fmin}^{fmax} X(m)$$

is the sum of the power spectrum within the physiologically relevant range (such that fmin is for example 0.1 Hz and fmax is for example 0.75 Hz or 1.0 Hz), and $$\sum_{i=1}^{n} X(m_i)$$

is the sum of the series of the n largest, continuous points within the frequency range where $m_1$ is the first point and $m_n$ is the last point in the sequence. n may take various values, for example 3, 4 or 5.

Figure 1:
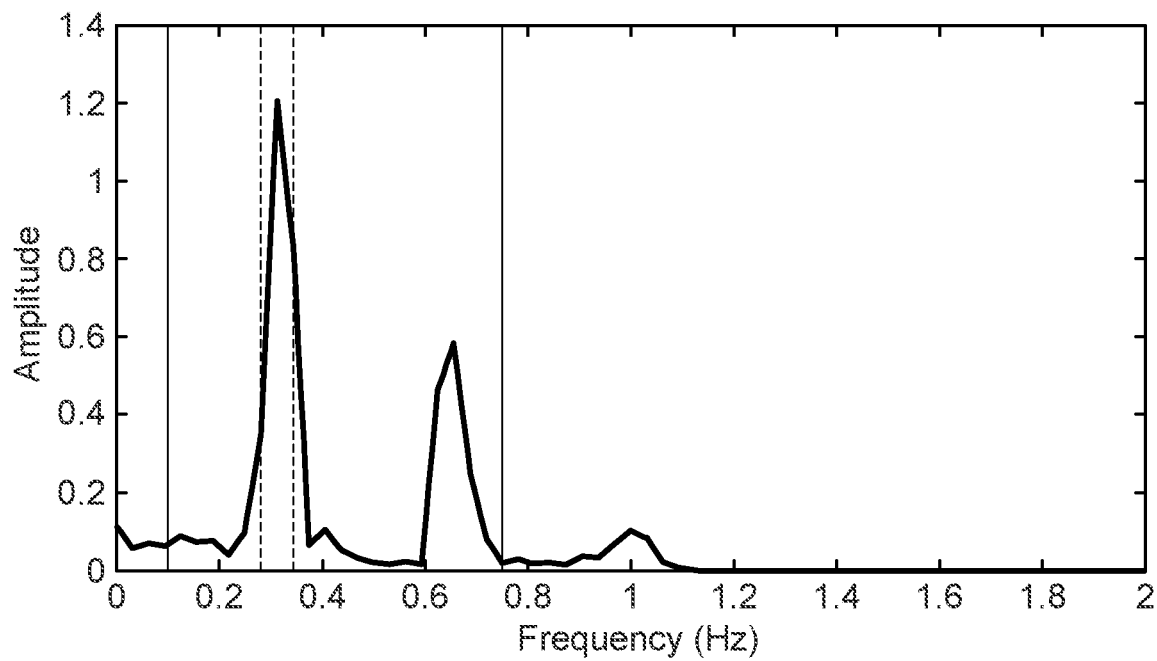
FIG. 1 illustrates an example fast-Fourier transform (FFT) for an extracted modulation from one time window, x(n). The solid curve is the FFT frequency spectrum. The solid vertical lines represent the region from 0.83 Hz to 1 Hz where the total respiratory area (TRA) is calculated. The dotted vertical lines represent the region of the maximum peak area (MPA) representing the largest three points clustered around the largest point in the FFT.

Ultimately, the $RQI_{FFT}$ gives a value of zero to one where the closer the value is to one the stronger the dominant frequency within the frequency range is. It is assumed that the larger the dominant frequency is within the frequency range, the stronger the given modulation is for that time window (i.e. for the extracted modulation corresponding to the time window and modulation mode) and the higher confidence there is in the estimation of the frequency of the periodic physiological process that is made using that extracted modulation (modulation mode and time window). An example of an FFT and the regions representing the MPA and TRA are shown in FIG. 1.

Autoregression RQI

In an embodiment, the obtaining of the quality parameter for each extracted modulation in each time window comprises evaluating a pole of an autoregressive model representing a dominant frequency component in the extracted modulation.

While both autoregressive modelling and the FFT can be used to derive the major frequency components of a waveform, autoregression is distinct from FFT because it provides a smoother, more exact interpretation of the frequency components and can be run on smaller time windows; however a major disadvantage of the autoregression function is determining the most advantageous model order to use. The autoregression function is a means to predict the current value in a time series based on the past values from the series plus an error term. In essence, the autoregression function can be viewed as a set of autocorrelation functions for every point x(n) in a series based on the previous x(n−i) terms and is defined as:

$$x(n) = \sum_{i=1}^{M} a_i x(n-i) + e(n)$$

where x(n) is the current value in the series, $a_i, \ldots a_M$ are the weighting coeffcients, x(n−i) ... x(n−M) are the previous terms in the series, e(n) is the error term, and M is the model order which represents how many previous terms are used in predicting x(n). In practice, the weighting coeffcients, $a_i \ldots a_M$, are most often obtained using the Yule-Walker equation, defined as:

$$a_{opt} R^{-1} r$$

where $a_{opt}$ are the ideal weighting coefficients as set by $R^{-1}$, the autocorrelation matrix and r, the autocorrelation vector (see R. Takalo, H. Hytti, and H. Ihalainen. Tutorial on univariate autoregressive spectral analysis. J Clin Monit Comput, 19(6):401-10, 2005. Takalo, Reijo Hytti, Heli Ihalainen, Heimo Journal Article Netherlands J Clin Monit Comput. 2005 December; 19(6):401-10. Epub 2006 Jan. 25). The ideal weighting coefficients, which define a function that recreates the observed signal x(n), can be used to define the transfer function H(ejω) which can further be used to define X(ω), the input sequence polynomial, the roots of which are the poles of the AR model which represent the dominant frequency components of the original signal x(n).

Figure 2:
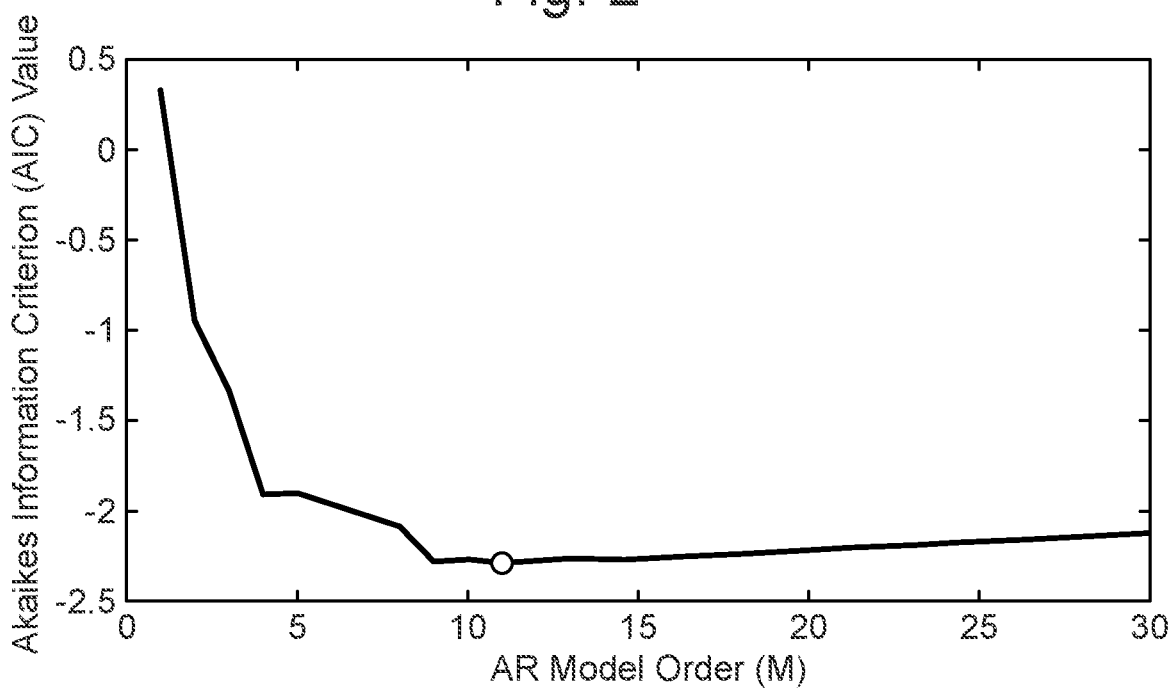
FIG. 2 is a representation of Akaike's Information Criterion (AIC) versus autoregression model order, M. The ideal model order (represented by the solid circle dot) is selected as the point where the AIC is minimized.
Figure 3:
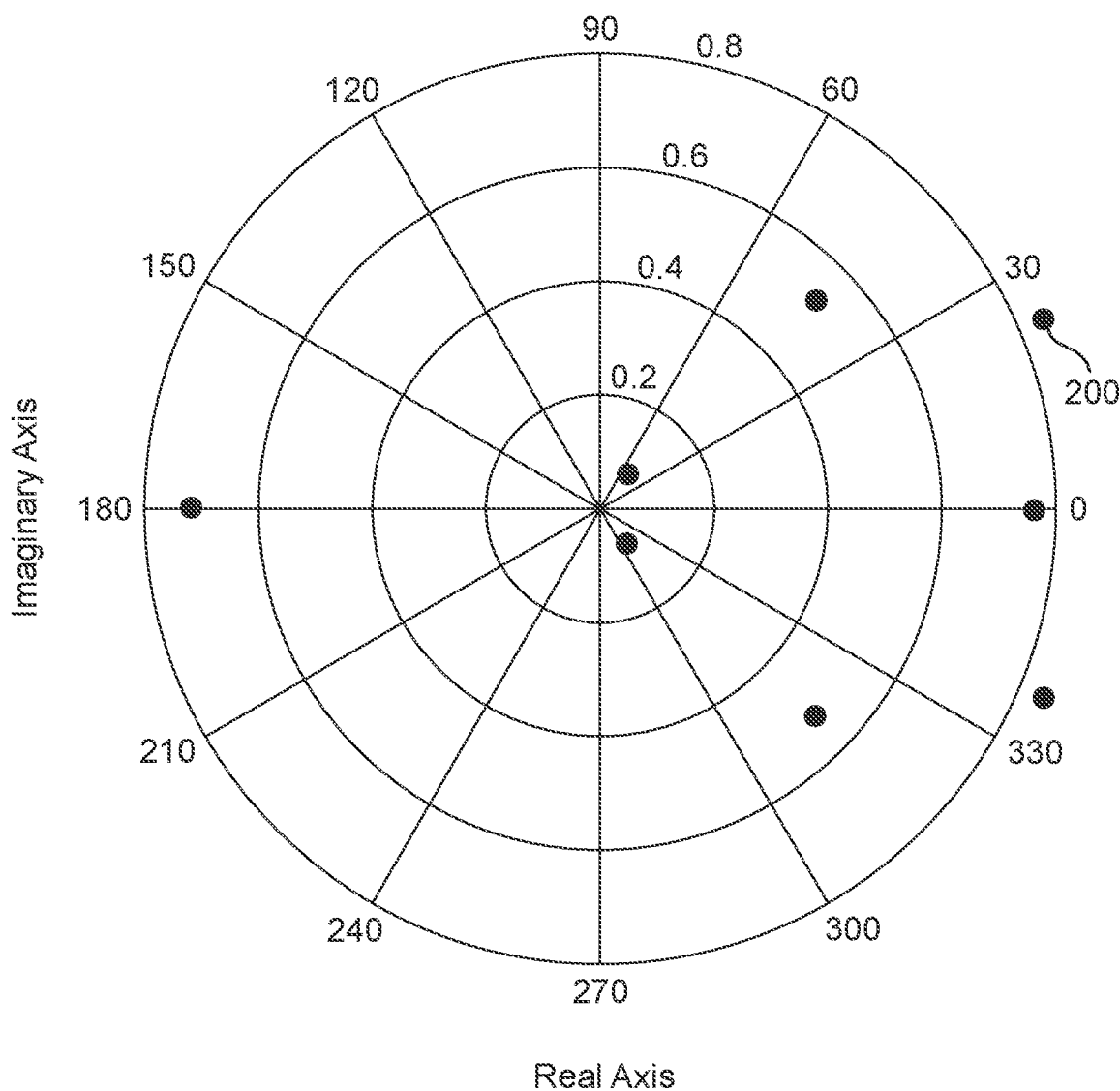
FIG. 3 is a plot of the autoregression poles (plot includes conjugate pairs) for an example window, x(n). An Autoregression RQI (RQIAR) is selected as the pole with the largest magnitude from the first two quadrants that falls within a range from 5 breaths/min to 60 breaths/min (marked 200). In the event that the largest pole falls outside of that range, the RQIAR is set to zero.

Based on these features of the autoregression function, the autoregression-based quality parameter (which may be referred to as $RQI_{AR}$) is defined using similar logic to the $RQI_{FFT}$. The quality parameter seeks to assign a value to each window of data x(n) (corresponding to the extracted modulation for a given modulation mode in the time window) based on the strength of the dominant frequency component in that signal. However, one of the shortcomings of autoregression is selecting the model order, M. This is particularly pertinent in this instance when the $RQI_{AR}$ will be applied uniformly to each x(n) where these x(n) represent data from different devices (ECG or PPG), different datasets, different patients, and different modulation modes. In order to address the possibility that no single model order would be suitable for this wide range of data, the autoregression for each window of data, x(n), was calculated for model orders M=1 to 30. Then the optimum model order for each specific window of extracted modulation, x(n), was selected by choosing the model order that returned the minimal Akaike's Information Criterion (AIC). The AIC is defined as:

$$AIC = \log\left(e * \left(1 + \frac{2M}{N}\right)\right)$$

where e is the error term for the model, M is the model order, and N is the total number of data points in x(n). The AIC works to find the ideal model order for a given set of data by returning higher AIC values for large error terms and large model orders; thus the ideal model order is one that has minimized the combination of the error and model order (FIG. 2). Using the ideal model that is specifically determined for each x(n), the $RQI_{AR}$ is determined by selecting the root of the polynomial in the denominator of the AR process transfer-function, with the largest magnitude in the positive frequency range similar to the methodology used by Cazares et al. (S. Cazares, M. Moulden, W. G. Redman, and L. Tarassenko. Tracking poles with an autoregressive model: a confidence index for the analysis of the intrapartum cardiotocogram. Med Eng Phys, 23(9):603-14, 2001. Cazares, S Moulden, M Redman, W G Tarassenko, L Research Support, Non-U.S. Gov't Research Support, U.S. Gov't, Non-P.H.S. England Med Eng Phys. 2001 November; 23(9): 603-14) (see FIG. 3). The magnitude of this root is used as the $RQI_{AR}$ if the frequency of the pole falls within a predetermined frequency range, for example 0.083 Hz to 1 Hz (5 breaths/min to 60 breaths/min) range and if it fall outside of this range, the $RQI_{AR}$ is set to zero (as it was determined that the noise of the signal outside of the frequency range of interest was likely too large to allow for an accurate estimation). In a similar fashion as the $RQI_{FFT}$, the values of the $RQI_{AR}$ closest to one represent the signals where there is a dominating frequency within the frequency range of interest and likely represent the signals where the best estimations can be made.

Autocorrelation RQI

In an embodiment, the obtaining of the quality parameter for each extracted modulation in each time window comprises evaluating a maximum autocorrelation between copies of the extracted modulation in the time window that are shifted in time relative to each other.

While the autoregression function can be thought of as a series of autocorrelation functions used to explain a single datapoint, it is also possible to define a simplified RQI using the autocorrelation function with lag times defined over the entire range of the signal. In an embodiment, the autocorrelation function is defined as:

$$r_k \frac{c_k}{c_0}$$

where $r_k$ is the autocorrelation value, $c_0$ is the sample variance, and:

$$c_k \frac{1}{N-1} \sum_{n=1}^{N-k} (x(n) - \bar{x}) * (x(n+k) - \bar{x})$$

where N is the total length of the sample, and $\bar{x}$ represents the mean of the sample. When the quality parameter is generated using an autocorrelation function it is referred to herein as the $RQI_{AC}$.

Figure 4:
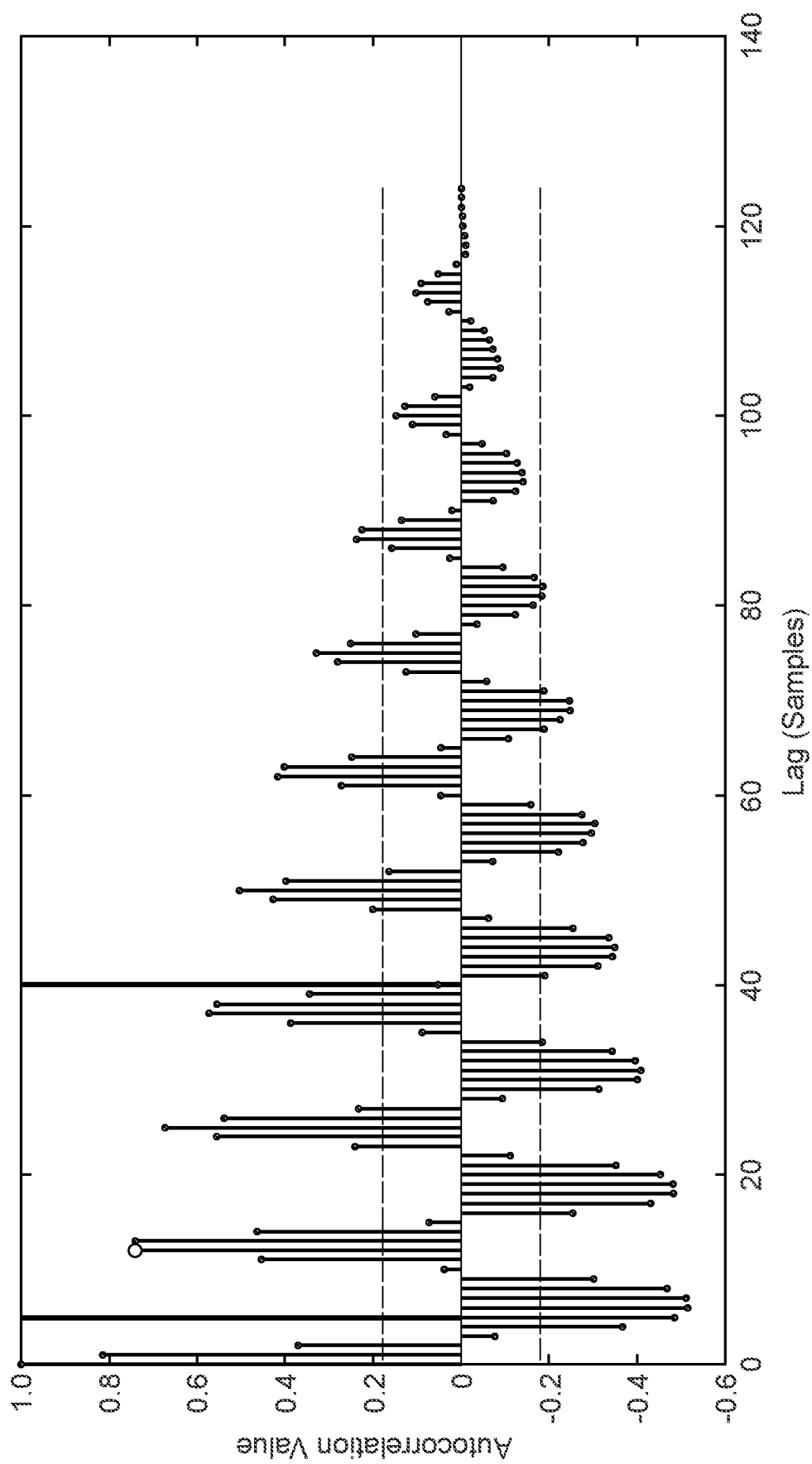
FIG. 4 is a plot of the autocorrelation of one window a(n) when considering an Autocorrelation RQI (RQIAC). Autocorrelation value represents the alignment of the original signal and the lagged signal where unity represents perfect autocorrelation. The vertical bars represent the largest autocorrelation between a lag of 5.33 samples and 40 samples (which corresponds to 1.33 seconds and 10 seconds at a sampling rate of 4 Hz).

The function may be scaled for unity such that when the lag of k is zero, the autocorrelation value is one indicating a perfect alignment of the two signals. For every other alignment the autocorrelation value is between zero and one. In the instance where a perfect sinusoid is present, when the lag, k, is as long as the period of the sinusoid, the autocorrelation value would again reach one. It is this principle that the autocorrelation RQI ($RQI_{AC}$) is based on. The $RQI_{AC}$ calculates the autocorrelation of an extracted modulation for a time window x(n) for every lag time in the signal, from k=0 . . . (N−1). Under the assumption that the modulation from the periodic physiological process is expected to be sinusoidal, the $RQI_{AC}$ selects the maximum autocorrelation within the lag range of a minimum k seconds (e.g. k=1.333 seconds, representing 6 breaths/min) to a maximum k seconds (e.g. k=10 seconds, representing 60 breaths/min). The $RQI_{AC}$ is then assigned to be the autocorrelation value of the specified k value because this represents the point where the signal most closely mirrors itself and thus the closer the value is to one at this point, the more sinusoidal the signal and the more likely it is that an accurate frequency of the periodic physiological process can be extracted from this time window (i.e. the extracted modulation corresponding to the time window and modulation mode) (FIG. 4).

Hjorth Parameter RQI

In an embodiment a quality parameter based on a Hjorth parameter can be used, referred to as $RQI_{HC}$ (Hjorth Complexity). Hjorth parameters were first defined in 1970 as a set of descriptive statistics looking to define the amplitude and time pattern qualities of a signal (B. Hjorth. Eeg analysis based on time domain properties. Electroencephalogr Clin Neurophysiol, 29(3):306-10, 1970. Hjorth, B Journal Article Netherlands Electroencephalogr Clin Neurophysiol. 1970 September; 29(3):306-10). Three Hjorth parameters have been defined: activity, mobility, and complexity. Activity, often referred to as the variance or mean power, is a measure of the squared standard deviation of a signal's amplitude. Mobility, known as the mean frequency, is the standard deviation of the slope with reference to the activity. Finally, complexity is a measure of the "softness" of a curve where the "most soft" curve is the sinusoid which has a complexity value of unity. The three Hjorth parameters can be calculated as follows:

$$\text{Activity} = m_0 = f(t)$$

$$\text{Mobility} = \sqrt{\frac{m_2}{m_0}} = \frac{d(f)}{dt}$$

$$\text{Complexity} = \frac{\sqrt{\frac{m_4}{m_2}}}{\sqrt{\frac{m_2}{m_0}}} = \frac{d^2(f)}{dt^2}$$

where $m_0$, $m_2$ and $m_4$ represent the zeroth, second, and fourth spectral moments, respectively of the signal and f(t) represents the curve as a function of time. Again making the assumption that the ideal waveform of the periodic physiological process would be a perfect sinusoid, the Hjorth parameter of interest for the Hjorth RQI ($RQI_{HC}$) is complexity. Similar to the other RQIs, when the Hjorth complexity parameter is closest to one it represents the most sinusoidal signal. Thus for each window of extracted modulation, x(n), the windows with the highest Hjorth complexity are expected to be the most sinusoidal and thus are expected to be the most likely to give an accurate estimation of the frequency of the periodic physiological process.

Pulmonary Modulation of the Cardiac System

In understanding the different organ systems in the body, they are often compartmentalized and simplified; however, the functioning of one organ system often has non-trivial effects on another. This is particularly the case with the cardiac and pulmonary systems. The cardiac and pulmonary systems are the two primary organ systems present in the thoracic cavity and function chiefly to transport oxygen and other nutrients into and carbon dioxide and other waste out of the body. As a result of this shared function, the cardiac and pulmonary systems are highly modulated by each other both through physical and nervous means.

Respiratory Modulation Via Nervous Control

The nervous system, particularly the autonomic nervous system, is known to play a major role in the coordination of the pulmonary and cardiac systems. One of the most prominent and widely studied interactions of the pulmonary and cardiac systems via the autonomic nervous system is respiratory sinus arrhythmia (RSA). RSA is a phenomenon by which the beat to beat heart rate interval is shortened during inspiration and lengthened during expiration. This manifests through activation of the pulmonary stretch receptors during inspiration. Once activated the pulmonary stretch receptors send inhibitor projections to the cardiac vagal neurones (CVNs) within the medulla oblongata of the brain. Normally, the CVNs send inhibitory signals to the heart to slow heart rate, but the signals from the pulmonary stretch receptors cause inhibition of the CVNs signals resulting in the elevated beat to beat rate that is observed in RSA. It is hypothesized that the function of RSA is to improve gas exchange efficiency. This is because the instantaneous blood volume circulation is increased during the brief period where the heart rate is elevated which is ideal when inspiration is at its peak as the alveoli in the lungs will be maximally inflated and able to participate in maximum gas exchange. Importantly, the prevalence and magnitude of RSA has been shown to be easily affected and reduced by poor cardiopulmonary function and disease (such as coronary artery disease), old age (RSA is very prominent in infancy but declines after), and poor physical fitness (both athletes and people who routinely exercise have higher prevalence of RSA than people who do not exercise).

The nervous system, particularly the autonomic nervous system, is known to play a major role in the coordination of the pulmonary and cardiac systems. One of the most prominent and widely studied interactions of the pulmonary and cardiac systems via the autonomic nervous system is respiratory sinus arrhythmia (RSA). RSA is a phenomenon by which the beat to beat heart rate interval is shortened during inspiration and lengthened during expiration. This manifests through activation of the pulmonary stretch receptors during inspiration. Once activated the pulmonary stretch receptors send inhibitor projections to the cardiac vagal neurones (CVNs) within the medulla oblongata of the brain. Normally, the CVNs send inhibitory signals to the heart to slow heart rate, but the signals from the pulmonary stretch receptors cause inhibition of the CVNs signals resulting in the elevated beat to beat rate that is observed in RSA. It is hypothesized that the function of RSA is to improve gas exchange efficiency. This is because the instantaneous blood volume circulation is increased during the brief period where the heart rate is elevated which is ideal when inspiration is at its peak as the alveoli in the lungs will be maximally inflated and able to participate in maximum gas exchange. Importantly, the prevalence and magnitude of RSA has been shown to be easily affected and reduced by poor cardiopulmonary function and disease (such as coronary artery disease), old age (RSA is very prominent in infancy but declines after), and poor physical fitness (both athletes and people who routinely exercise have higher prevalence of RSA than people who do not exercise).

Respiratory Modulation Via Physical Mechanisms

In addition to modulation via the nervous system, the major changes in pressure and size in the thoracic cavity caused by respiration have effects that alter the cardiac system. There are three major modulations caused by these physical changes: (1) decreased stroke volume (left ventricular output), (2) increased blood flow from the periphery to the thoracic cavity, and (3) changes in heart position within the thoracic cavity.

(1) Decreased Stroke Volume

The decreased stroke volume noted during inspiration is caused by several factors. The primary factor is that the negative pressure in the thoracic cavity that is created causes distension of the pulmonary vessels which leads to blood pooling in these vessels. Additionally, the pulmonary capillaries are compressed due to the expansion of the alveoli causing reduced return to the left ventricle and the expansion of the right ventricle during inspiration causes impingement in the left ventricle by the intra-ventricular septum.

(2) Increased Blood Flow into the Thoracic Cavity

This is caused by two mechanisms. The first is due to the decrease in intrathoracic pressure. The pressure drop in the intrathoracic cavity causes an equivalent drop in pressure in the intrathroacic blood vessels causing increased flow to those vessels. Additionally, the lowering of the diaphragm causes abdominal compression and increases in pressure in the intra-abdominal veins thus exacerbating the pressure differential and leading to blood flow into the thoracic cavity.

(3) Changes in Heart Position within Thoracic Cavity

The proximity of the lungs to the heart means that during inspiration when the lungs are expanding, they cause a shift in the positioning of the heart within the thoracic cavity. MRI studies of this effect have found that movement is on average 12.4+/−5.9 mm downward in the cranio-caudal axis, 4.3+/−3.7 mm in anterior direction on the anterior-posterior axis, and 2.0+/−2.1 mm rightward on the left-right axis. Additionally, some rotational effects were seen; however, this was highly variable.

Observable Modulations of Respiratory System in ECG and PPG Waveforms

ECG and PPG are both capable of acquiring the respiratory signal from the cardiac signal. However, the two technologies use different physiological measurements to acquire this information and thus it is as a result of different modulations that the respiratory rate can be derived from the ECG and PPG.

Acquisition of Respiratory Rate: ECG

The ECG functions by converting the ionic current produced by the body during the heart cycle into electron current that can be recorded by electrically conductive electrodes placed on the surface of the body. Ultimately, the voltage drop across the thorax caused by the heart beat is detected and can be used to monitor all phases of the heart cycle and cardiac abnormalities such as the presence of arrhythmia, ischemia, and infarction. In order for the ECG to be used to monitor respiration, the respiratory modulations on the heartbeat must manifest as observable changes in the heart's electrical signal. Two of the physiological modulations previously noted: cardiac movement within the thoracic cavity and RSA cause observable changes in the ECG that can be used for monitoring respiratory rate.

Cardiac Movement within the Thoracic Cavity

As has previously been described, the heart moves within the thoracic cavity during respiration. In addition to this effect, the electrodes used to measure the ECG change in their position relative to the heart which also has an effect on the overall ECG. These two effects cause an observable modulation on the mean electrical axis (MEA) of the ECG and in addition to effects caused by the changing thoracic impedance due to the lungs filling with air cause a change in both R-wave peak amplitude (RPA) and R-wave area (RWA). Comparisons of multiple lead ECG data can be used to acquire the respiratory signal. Alternatively, respiratory information can be extracted using only a single lead ECG.

Respiratory Sinus Arrhythmia (RSA)

As RSA is a nervous system response that physically alters when the AV node in the heart initiates a heartbeat, the RSA modulation on the ECG is obtained by detecting the peak of each QRS complex of the ECG and using these points to obtain the heart rate variability. Due to the respiratory rate synchronized instantaneous cycling of bradycardia and tachycardia observed in the instantaneous heart rate, it is possible to use the ECG to detect respiratory rate by plotting the length of each R—R interval at the instant in time that it was observed. The validity of detecting RSA from ECG as a means for detecting respiratory rate has been widely reported.

Acquisition of Respiratory Rate: PPG

The PPG functions by measuring the light reflectance or transmission of red (660 nm) and infrared (940 nm) light from an LED to a photoelectric cell. Reflectance PPG places the LED and photoelectric cell side by side anywhere on the body, but most often on appendages such as the arm, while transmission PPG places the LED on opposite sides of the body on small appendages such as the finger and earlobe. While the PPG is most often used to measure $SpO_2$ due to the varying extinction coefficients of haemoglobin and oxyhaemoglobin in the infrared spectrum, it can also be used to obtain a heartbeat signal through observation of the absorption of red light through time. This is because the light absorbing coefficient of the haemoglobin in blood is higher than the surrounding tissues. Thus as the volume of blood increases in the circulatory system due to a heartbeat, it causes a decrease in the amount of light that passes through the body and is detected by the photoelectric cell giving a measurable heart rate signal. Through the physiological modulations of the heartbeat discussed previously, the PPG heart rate signal can be used to acquire the respiratory signal through three techniques: respiratory-induced amplitude variation (RIAV), respiratory-induced intensity variation (RIIV), and respiratory-induced frequency variation (RIFV).

Respiratory-Induced Amplitude Variation (RIAV)

RIAV is the noted decrease in peak-to-trough length during inspiration compared to exhalation. The RIAV observed in the PPG signal is caused by the decreased stroke volume output by the heart during inspiration. As previously mentioned, during inspiration, the rate of cardiac filling is lessened resulting in a small cardiac output which results in the observable decrease in peak-to-trough length during inspiration as compared to during exhalation.

Respiratory-Induced Intensity Variation (RIIV)

The RIIV can be observed in the PPG as the fluctuation of the peak amplitude heights in the PPG. The RIIV signal is not thought to be directly linked with the heartbeat itself, but rather is a unique physiological effect on the PPG that is correlated to respiratory rate through the downstream physiological effects of the changing pressure in the thoracic cavity. Ultimately, it is thought that the RIIV is the result of one or a combination of three effects. The first is the increase in venous return to the thoracic cavity due to both the increased pooling of blood in the pulmonary veins and the increased flow out of the abdominal veins due to compression of the abdominal cavity by the diaphragm. The second effect is due to changes in arterial transmission. The final effect is due to the nervous system directed vasoconstriction of the venous system leading to reduced blood volume during inhalation.

Respiratory-Induced Frequency Variation (RIFV)

Similar to the effect of RSA on the ECG, RIFV is the difference in instantaneous heart rate observed in the PPG due to respiratory sinus arrhythmia. It can be monitored in the PPG in the same way by noting the differences in the time length between peaks in the PPG.

Detailed Examples and Performance

This section provides details about performance of embodiments of the invention.

Data Sets

Data were obtained for this analysis from two publicly available sources: CapnoBase and MIMIC II (W. Karlen, M. Turner, E. Cooke, G. A. Dumont, and J. M. Ansermino. Capnobase: Signal database and tools to collect, share and annotate respiratory signals. In Annual Meeting of the Society for Technology in Anesthesia (STA), West Palm Beach, page 25; and M. Saeed, M. Villarroel, A. T. Reisner, G. Clifford, L. W. Lehman, G. Moody, T. Heldt, T. H. Kyaw, B. Moody, and R. G. Mark. Multiparameter intelligent monitoring in intensive care ii: a public-access intensive care unit database. Crit Care Med, 39(5):952-960, 2011).

Both data sets contained simultaneous PPG and ECG data, and either capnography or impedance plethysmography (IP) data, which are used to obtain a "gold standard" respiration rate estimate.

1) CapnoBase:

This data set was collected from 59 pediatric (median age: 9, range 1-17 years) and 35 adult (median age: 52, range: 26-76 years) patients undergoing elective surgery or routine anaesthesia.

The inventors used the data set described in W. Karlen, S. Raman, J. M. Ansermino, and G. A. Dumont. Multiparameter respiratory rate estimation from the photoplethysmogram. Biomedical Engineering, IEEE Transactions on, 60(7):1946-1953, 2013. This data set contains one high-quality, eight-minute segment (an example of the stream of data 20 referred to above with reference to FIG. 10) with simultaneous PPG, ECG, and capnography waveform data for each of 42 patients (29 pediatric and 13 adult). Expertly annotated breaths from the capnography waveforms were used to define a reference respiration rate estimate when using our method with the PPG and ECG.

2) MIMIC II:

This data set contains patient records for over 25,000 patients in four ICU units: medical, surgical, cardiac, and cardiac surgery. For this analysis, only records containing waveform data were used. This subset consisted of 1017 adult patients (median age: 66, range: 18-91 years). For these patients, a single eight-minute segment (an example of the stream of data 20 referred to above with reference to FIG. 10) containing PPG, ECG, and impedance plethysmography (IP) (or the subset of these when not all three signals were recorded) was extracted between the 60th and 68th minute after recording began. This ensured that any artefact that arose at the start of the monitoring period was omitted. The IP was used to obtain a reference respiration rate estimate; however, since the IP waveforms were not expertly annotated, in instances where the IP waveforms were noisy, the reference estimate was likely to be wrong. To overcome this, two benchmark respiration rate estimation algorithms were used to assess the respiration rate from the IP data. These were 1) ARSpec (S. A. Shah, S. Fleming, M. Thompson, and L. Tarassenko. Respiratory rate estimation during triage of children in hospitals. Journal of Medical Engineering & Technology, 39(8):514-524, 2015); and
2) an FFT-based algorithm (W. Karlen, S. Raman, J. M. Ansermino, and G. A. Dumont. Multiparameter respiratory rate estimation from the photoplethysmogram. Biomedical Engineering, IEEE Transactions on, 60(7):1946 1953, 2013.).

When the algorithms agreed within ≤2 breaths/min, the estimates were averaged to give the reference respiration rate and when the algorithms differed by >2 breaths/min, it was assumed that a reliable reference respiration rate could not be obtained, and the segment was not analysed.

Waveform Extraction

After creating the unique 32 second windows for each patient, the peaks and troughs of the PPG or the Q wave minimum and R wave maximum of the ECG (referred to above as identifying the reference features) were extracted and used to obtain (extract) the associated respiratory modulations. For the CapnoBase dataset, these points are provided and have been validated by an expert rater. For the MIMIC II database, the PPG peaks and troughs are calculated using a delineator described by Li et al. (Bing Nan Li, Ming *Chui* Dong, and Mang I. Vai. On an automatic delineator for arterial blood pressure waveforms. Biomedical Signal Processing and Control, 5(1):76-81, 2010.) that has been adapted for PPG and is based on using a combinatorial analysis of the PPG waveforms their derivatives. For ECG, the R wave peaks are found using the Pan-Tompkins algorithm and the Q wave troughs are found by selecting the waveform minimum 200 ms prior to the R wave peak. These peak and trough features are then used to extract three unique waveforms for PPG (RIAV, RIIV, and RIFV) and ECG (RSA, RPA, and RWA). The unique time series that is created for each waveform is then resampled to a uniform grid of 4 Hz.

RIAV and RWA may also be referred to as amplitude modulation (AM). RIFV and RSA may also be referred to as frequency modulation (FM). RIIV and RPA may also be referred to as baseline wander (BW). Extraction of the respiration waveforms representing the respiration modulations, AM, FM, and BW, from the PPG and ECG using peak-trough detection in the time domain is described in D. J. Meredith, D. Clifton, P. Charlton, J. Brooks, C. W. Pugh, and L. Tarassenko. Photoplethysmographic derivation of respiratory rate: a review of relevant physiology. Journal of medical engineering & technology, 36(1):1-7, 2012. The peaks are represented as a series of pairs, $(t_{pk,i}, y_{pk,i})_{i \ldots N_{pk}}$, as are the troughs, $(t_{tr,i}, y_{tr,i})_{i \ldots N_{tr}}$. The respiratory amplitude modulation (AM) is the height of the signal from the peak to the corresponding trough, $y_{AM} = (t_{pk,i}, y_{pk,i} - y_{tr,i})_{i \ldots N_{pk}}$, where $t_i$ is taken to be the time of the peak pair. The frequency modulation (FM) is the change in time interval between peaks, $y_{FM} = (t_{pk,i}, t_{pk,i+1} - t_{pk,i})_{i \ldots N_{pk-1}}$. The baseline wander (BW) is the envelope of the original signal, $y_{BW} = (t_{pk,i}, y_{pk,i})_{i \ldots N_{pk}}$. These modulations were extracted by segmenting each 8-minute data segment into 15 non-overlapping windows of 32s length. Each modulation was extracted for every window, resulting in 3 respiratory waveforms (AM, FM, and BW) for each window of the original sensor data. Each respiratory waveform was then filtered with a 5th-order Butterworth IIR bandpass filter between 0.83 and 1 Hz and subsequently downsampled to 4 Hz.

Evaluation and Comparison

The RQIs were evaluated by using the existing ARSpec algorithm to estimate respiration rate for each of the three modulations extracted from each window of PPG or ECG data. The absolute difference in the respiratory estimate between this and the reference respiration rate estimate (from either capnography or IP, depending on the data set) was taken as a proxy for the quality of the respiratory information contained for a particular modulation in a given window. Each RQI was evaluated independently of this calculation and scaled such that the RQI values expected to indicate the best quality respiratory information (i.e., the respiration rate estimation that most closely matched the reference respiration rate value) were closest to 1 and the worst were closest to 0. The performance of each RQI was independently evaluated by sequentially calculating the mean absolute error (MAE) and standard error (SE) of the absolute difference of the estimate (from the existing ARSpec algorithm) and reference estimate (from capnography or IP) as the windows with the lowest RQI values were discarded. In practice, the MAE and SE were calculated for the entire data set (where every modulation and every window for each data set were analysed independently), and then the windows with the lowest RQI values were sequentially discarded, with the MAE and SE being recalculated after each discarding step. This process was repeated by discarding increments of 1% of the data, from lowest-RQI windows to highest. In addition to evaluating the RQIs against each other, the performance of the RQIs was compared to the use of an SQI defined in M. A. F. Pimentel, M. D. Santos, D. B. Springer, and G. D. Clifford. Heart beat detection in multimodal physiological data using a hidden semi-markov model and signal quality indices. Physiol Meas, 36(8):1717-1727, 2015. This represents the current state-of-the-art, in which respiration rate estimation is performed on windows of data with high SQI values. The "ideal" performance scenario was also considered, where the MAE and SE are incrementally calculated where the absolute difference of the ARSpec estimate and reference estimate is used to identify and then discard the poorest performing windows. The latter represents the best performance that could be achieved in the "ideal" situation in which the reference is available; in practice, the reference is unavailable-hence the need to estimate respiration rate from the PPG or ECG-data.

Results

Overall, a total of 1890 windows (100% of possible windows) were analysed for the CapnoBase PPG data, 1886 (99.8%) of CapnoBase ECG data, 32858 (71.8%) of MIMIC II PPG data, and 35784 (78.2%) of MIMIC II ECG data.

Windows were discarded prior to analysis for three reasons: (1) if, for the given window, either the reference waveform (capnography or IP) or the PPG/ECG was not available or did not contain usable data (i.e., a flat line signal); (2) if a reliable reference respiration rate could not be obtained (especially relevant in the noisy MIMIC II data set); or (3) if the peak and trough detectors detected ≤2 peaks/troughs, indicating an unusable set of respiratory modulations for a window.

The performance of the RQIs can be best understood by observing the change in the MAE as increasingly higher quality data is retained while lower quality data is discarded. TABLE I below displays the difference of the MAE for 100% and 50% data retention ($MAE_{100}-MAE_{50}$) and the standard error of the difference of the MAE.

TABLE I

DIFFERENCE BETWEEN $MAE_{100}$ AND $MAE_{50}$

|  | CapnoBase | | MIMIC II | |
| --- | --- | --- | --- | --- |
|  | PPG | ECG | PPG | ECG |
| $RQI_{FFT}$ | 4.17 ± 0.10 | 3.83 ± 0.12 | 3.49 ± 0.03 | 3.79 ± 0.03 |
| $RQI_{AC}$ | 4.33 ± 0.10 | 4.95 ± 0.11 | 3.09 ± 0.03 | 3.12 ± 0.03 |
| $RQI_{AR}$ | 3.49 ± 0.11 | 3.33 ± 0.12 | 2.36 ± 0.03 | 2.23 ± 0.03 |
| $RQI_{HC}$ | 3.02 ± 0.11 | 3.00 ± 0.12 | 3.32 ± 0.03 | 3.44 ± 0.03 |
| SQI | 0.47 ± 0.12 | 0.76 ± 0.13 | 0.93 ± 0.03 | 0.49 ± 0.03 |
| Control | 5.61 ± 0.07 | 7.14 ± 0.08 | 8.41 ± 0.02 | 9.20 ± 0.02 |

The largest difference between $MAE_{100}$ and $MAE_{50}$ for CapnoBase was seen when using $RQI_{AC}$ for both PPG (4.33±0.10) and ECG (4.95±0.11). All RQIs substantially improved on the performance of using the SQI for PPG (0.47±0.12) and ECG (0.76±0.13). Furthermore, the best performing RQI for MIMIC II was $RQI_{FFT}$ for both PPG (3.49±0.03) and ECG (3.79±0.03). Additionally, all RQIs outperformed the SQI in both PPG (0.93±0.03) and ECG (0.49±0.03).

Figure 5:
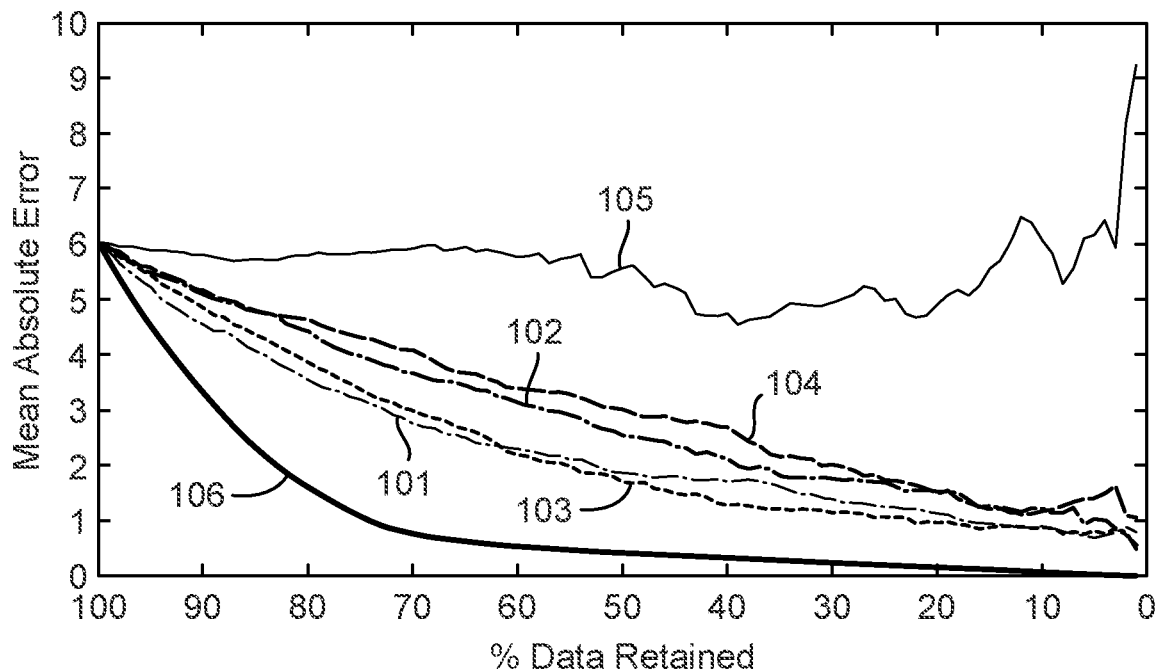
FIG. 5 is a plot showing performance of RQIs and SQI on the CapnoBase dataset using PPG data and using an ARSpec estimation algorithm to determine the absolute difference of the respiration rate estimation from the standard. Performance is displayed as the mean absolute error (MAE) values for each quality parameter (RQI) as the poorest quality data is sequentially removed.
Figure 6:
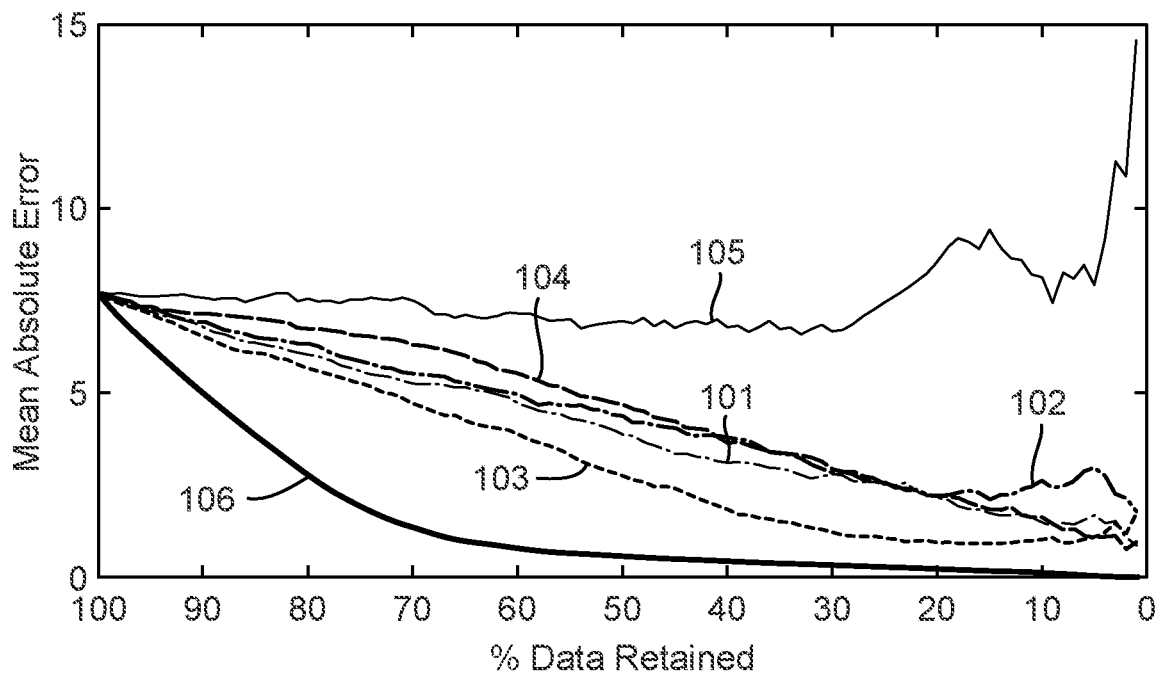
FIG. 6 is plot showing performance of RQIs and SQI on the CapnoBase dataset using ECG data and using the ARSpec estimation algorithm to determine the absolute difference of the respiration rate estimation from the standard. Performance is displayed as the mean absolute error (MAE) values for each quality parameter (RQI) as the poorest quality data is sequentially removed.

The performance of each RQI at each 1% data discard increment is shown in FIG. 5 (CapnoBase PPG), FIG. 6 (CapnoBase ECG), FIG. 7 (MIMIC II PPG), and FIG. 8 (MIMIC II ECG). These plots show a steady trend in decreasing MAE for each RQI as the data with the poorest performing RQI values are discarded. Furthermore, these plots also indicate that each RQI outperforms the SQI regardless of how much data is discarded.

One of the biggest challenges in estimating respiration rate from PPG and ECG is ensuring the quality of the respiratory signal from which the estimation will be made. Embodiments of the invention address this challenge by applying novel pre-processing steps to different extracted modulation. Four RQIs were found to be particularly effective, designed and validated based on the assumption that for small timescales the respiratory waveform is periodic.

The above results highlight a few key findings. The first is the general usefulness of using RQIs. While the $RQI_{AC}$ and $RQI_{FFT}$ outperformed the other two RQIs, every RQI improved substantially on the ability of the SQI to distinguish between high-quality and low-quality respiratory signals. This suggests that the implementation of the RQI pre-processing step improves the accuracy of respiration rate estimation algorithms. Furthermore, improvements in the MAE for even modest amounts of data discarded based on RQI performance are seen. This indicates the robustness gained by using RQIs, as they are not only capable of distinguishing high-quality data from low-quality data as a binary estimate, but provide a continuous scale as to the quality of the respiratory data in each particular window.

Furthermore, the inventors have shown that the robustness of the RQIs extends to a number of varied settings. Firstly, each RQI was applied to respiratory modulations obtained from both PPG and ECG data and each RQI performed similarly well on both. This provides support for the RQIs being generally applicable to any small-timescale respiratory waveform (e.g., when estimating respiration rate from video). The RQIs also demonstrated good performance as the data quality decreased. This can be seen in the distinction of the CapnoBase and MIMIC II data sets. The CapnoBase data set was obtained under idealised circumstances for otherwise healthy patients undergoing routine anesthesia or elective surgery; however, the MIMIC II data set was collected on a much larger patient cohort in four different ICUs. As a result, quality of the MIMIC II data is much lower than that of the CapnoBase as evidenced by the much larger amount of data discarded prior to analysis and the higher MAE at 100% data retention. While RQI performance decreased slightly when applied to the MIMIC II data set compared to the CapnoBase data set, it exhibited the same general trends and was still able to effectively discard the poorest quality data.

The overall performance of each RQI vastly improved on the performance of the SQI; however, further improvement in the RQIs can be made by fusing each RQI into a single metric. The fused RQI can outperform each individual RQI and obtain results even more closely resembling the performance of the "ideal" metric.

We claim:

1. A system for determining the frequency of a periodic physiological process of a subject, comprising:
   a device, comprising:
      a data receiving unit configured to receive plural time windows of data representing physiological measurements on the subject;
      a data processing unit; and
      a sensing system configured to perform the physiological measurements on the subject; and
   a data processing station connectable via a network to the device, wherein:
   the data processing unit is configured to:
      identify reference features corresponding to one or more modulation modes of the physiological measurements in each of the time windows;
      for each modulation mode, extract a modulation of the corresponding reference features in each time window, thereby obtaining an extracted modulation for each combination of modulation mode and time window;
      process each extracted modulation to obtain a quality parameter for each combination of modulation mode and time window, the quality parameter for each extracted modulation representing how strongly the extracted modulation exhibits a waveform of the periodic physiological process; and
      process all or a subset of the extracted modulations to calculate the frequency of the periodic physiological process of the subject, wherein:
         the frequency of the periodic physiological process is calculated using only a subset of the extracted modulations, each extracted modulation of the subset being selected using the quality parameter for that extracted modulation,
         the frequency of the periodic physiological process is calculated using a combination of all of the extracted modulations, each extracted modulation having a weighting defined by the quality parameter of that extracted modulation, or the frequency of the periodic physiological process is calculated using only a subset of the extracted modulations, each extracted modulation of the subset being selected using the quality parameter for that extracted modulation, and the frequency of the periodic physiological process is calculated using a combination of the selected subset of extracted modulations, each one of the selected subset of extracted modulations having a weighting defined by the quality parameter of that extracted modulation;

and wherein:

the system is configured to distribute processing of each extracted modulation to calculate the frequency of a periodic physiological process of the subject between the device and the data processing station according to the quality parameter of the extracted modulation obtained by the device.

2. The system of claim 1, wherein the frequency of the periodic physiological process is a respiration rate.

3. The system of claim 2, wherein the physiological measurements comprise ECG measurements.

4. The system of claim 3, wherein the one or more modulation modes comprises one or more of the following: respiratory sinus arrhythmia, R-wave peak amplitude, and R-wave area.

5. The system of claim 3, wherein the reference features comprise one or more of the following: Q-wave minimum and R-wave maximum.

6. The system of claim 2, wherein the physiological measurements comprise PPG measurements.

7. The system of claim 6, wherein the one or more modulation modes comprises one or more of the following: respiratory-induced amplitude variation, respiratory-induced intensity variation, and respiratory-induced frequency variation.

8. The system of claim 7, wherein the reference features comprise one or more of the following: peaks of the PPG measurements and troughs of the PPG measurements.

9. The system of claim 1, wherein the frequency of the periodic physiological process is a heart rate.

10. The system of claim 1, wherein the physiological measurements comprise accelerometer measurements.

11. The system of claim 1, wherein the selecting of a subset of the extracted modulations is performed by selecting only those extracted modulations in which a strength of the waveform of the periodic physiological process is above a predetermined level, by comparing the quality parameters of each of the extracted modulations with a corresponding predetermined threshold value.

12. The system of claim 1, wherein the selecting of a subset of the extracted modulations is performed by selecting a predetermined proportion of the extracted modulations in descending order of a strength of the waveform of the periodic physiological process, as represented by the quality parameter of each extracted modulation.

13. The system of claim 1, wherein higher weightings are applied to extracted modulations having quality parameters representing higher strengths of the waveform of the periodic physiological process relative to extracted modulations having quality parameters representing lower strengths of the waveform of the periodic physiological process.

14. The system of claim 1, wherein for at least a portion of all of the time windows of data, different weightings are applied to extracted modulations corresponding to different modulation modes.

15. The system of claim 1, wherein the obtaining of the quality parameter for each extracted modulation, and therefore each combination of modulation mode and time window, comprises: Fourier transforming the extracted modulation in the time window and evaluating a property of the largest peak in a Fourier transform.

16. The system of claim 1, wherein the obtaining of the quality parameter for each extracted modulation, and therefore each combination of modulation mode and time window, comprises evaluating a root of a polynomial in a denominator of a transfer function for an autoregressive model representing a dominant frequency component in the extracted modulation in the time window.

17. The system of claim 16, further comprising determining an optimum model order for the autoregressive model for each extracted modulation.

18. The system of claim 1, wherein the obtaining of the quality parameter for each extracted modulation, and therefore each combination of modulation mode and time window, comprises evaluating a maximum autocorrelation between copies of the extracted modulation in the time window that are shifted in time relative to each other.

19. The system of claim 1, wherein the obtaining of the quality parameter for each extracted modulation, and therefore each combination of modulation mode and time window, comprises evaluating a Hjorth complexity.

20. The system of claim 1, wherein the obtaining of the quality parameter for each extracted modulation, and therefore each combination of modulation mode and time window, comprises a combination of one or more of the following: Fourier transforming the extracted modulation in the time window and evaluating a property of the largest peak in a Fourier transform; evaluating a root of a polynomial in a denominator of a transfer function for an autoregressive model representing a dominant frequency component in the extracted modulation in the time window; evaluating a maximum autocorrelation between copies of the extracted modulation in the time window that are shifted in time relative to each other; and evaluating a Hjorth complexity.

21. The system of claim 1, configured so that the distribution of processing is such that:

each extracted modulation having a quality parameter indicating that a strength of the waveform of the periodic physiological process in the extracted modulation is higher than a predetermined level is sent to the data processing station for processing; and each extracted modulation having a quality parameter indicating that the strength of the waveform of the periodic physiological process in the extracted modulation is lower than the predetermined level is processed by the device or discarded.

* * * * *